United States Patent [19]

Weithmann et al.

[11] Patent Number: 5,508,275
[45] Date of Patent: Apr. 16, 1996

[54] LIPID-SELECTIVE ANTIOXIDANTS AND THEIR PREPARATION AND USE

[75] Inventors: Klaus-Ulrich Weithmann, Hofheim am Taunus; Günther Wess, Erlensee; Dirk Seiffge, Mainz, all of Germany

[73] Assignee: Hoechst Aktiengesellschaft, Frankfurt am Main, Germany

[21] Appl. No.: 212,863

[22] Filed: Mar. 15, 1994

Related U.S. Application Data

[62] Division of Ser. No. 638,321, Jan. 7, 1991, Pat. No. 5,318, 987.

[30] Foreign Application Priority Data

Jan. 9, 1990 [DE] Germany .................. 40 00 397.3

[51] Int. Cl.$^6$ ................ A61K 31/56; A61K 31/385; A61K 31/165
[52] U.S. Cl. ............... 514/182; 514/436; 514/440; 514/456; 514/532; 514/545; 514/557; 514/544; 514/559; 514/558; 514/474; 514/616; 514/688; 514/718; 514/731; 514/618; 549/21; 549/22; 549/39; 549/218; 549/315; 549/374; 549/405; 552/544; 552/548; 560/15; 560/60; 564/155; 564/158; 564/192; 568/662; 568/766
[58] Field of Search ............... 549/405, 22, 374, 549/315, 218, 21, 39; 564/155, 158, 192; 560/15, 60; 568/662, 766; 552/544, 548; 514/182, 456, 474, 616, 688, 545, 436, 532, 718, 544, 731, 559, 557, 618, 558, 440

[56] References Cited

U.S. PATENT DOCUMENTS

| | | | |
|---|---|---|---|
| 3,910,888 | 10/1975 | Widauer et al. | 260/239.5 |
| 4,157,984 | 6/1979 | Zilliken | 252/407 |
| 4,232,122 | 11/1980 | Zilliken | 435/52 |
| 4,368,264 | 1/1983 | Zilliken | 435/52 |
| 4,939,128 | 7/1990 | Kato et al. | 514/82 |

FOREIGN PATENT DOCUMENTS

| | | |
|---|---|---|
| 0339486 | 11/1989 | European Pat. Off. . |
| PCT/US79/ 00346 | 10/1980 | WIPO . |

OTHER PUBLICATIONS

Simic et al., Oxygen Radicals in Biology and Medicine, Plenum Press (1988) pp. 1062–1064.
Halliwell et al., Free Radicals in Biology and Medicine, 2d ed., Clarendon Press (1989) pp. 336–337, 416, 417, 419 and 469.
Sevanian et al., "Cholesterol Epoxide Is A Direct–Acting Mutagen," Proc. Natl. Acad. Sci. 81:4198–4202 (1984).
Gilles et al., "Synthesis of New Fluorescent Spirolactone Derivatives: Determination of Their Affinities For Aldosterone Receptors," Steroids 51:465–69 (1988).
T. Takagi et al., "Antioxidant for Fats and Oils from Canary Seed: Sterol and Triterpene Alcohol Esters of Caffeic Acid," Journal of the American Oil Chemists' Society (JAOCS), Oct. 1980, pp. 326–330.
Chemical Abstracts, vol. 102, No. 21, May 27, 1985, Abstract No. 183925, H. Gunnar et al., "Flavor Changes in Whole Milk Powder During Storage. II. The Kinetics of The Formation of Volatile Fat Oxidation Products and Other Volatile Compounds".
C. Suarna et al., "Effect of Alcohols on the Oxidation of the Vitamin E Model Compound, 2,2,5,7, 8–Pentamethyl–6–Chromanol," Lipids, vol. 24, No. 1, Jan. 1989, pp. 56–60.
Chemical Abstracts, vol. 73, No. 3, Jul. 20, 1970, Abstract No. 15129, K. Suga et al., "Cholesterol Derivatives."Chemical Abstracts, vol. 110, No. 15, Apr. 10, 1989, Abstract No. 128615, H. Scholich et al., "Antioxidant Activity of Dihydrolipoate Against Microsomal Lipid Peroxidation and its Dependence on alpha–Tocopherol."Chemical Abstracts, vol. 110, No. 25, Jun. 19, 1989, Abstract No. 224834, E. Roldan et al., "Fundamentals and Applications of the Antioxidative Properties of Thioctic Acid."

*Primary Examiner*—C. Warren Ivy
*Assistant Examiner*—Amelia Owens
*Attorney, Agent, or Firm*—Finnegan, Henderson, Farabow, Garrett & Dunner

[57] ABSTRACT

Lipid-selective antioxidants of the formula I $$(A)_a(L)(X)_{a'} \qquad (I),$$

in which
 A=an antioxidative component,
 L=a bridging member,
 X=a lipophilic component
 a and a'=independently of one another the numbers 1 or 2.
The compounds are used for the protection of lipid-containing substances against oxidation and in pharmaceuticals for the prophylaxis and treatment of diseases in which bioradicals are involved, in particular of coronary, circulatory and vascular diseases.

13 Claims, No Drawings

LIPID-SELECTIVE ANTIOXIDANTS AND THEIR PREPARATION AND USE

This is a division of application Ser. No. 07/638,321, filed Jan. 7, 1991, now U.S. Pat. No. 5,318,987.

Antioxidants are used in the foodstuffs industry as preservative additives as foodstuffs can undergo undesired oxidative changes on storage. It is also known that the lipid components of the foodstuffs are particularly sensitive to oxidation and become rancid on storage in air as peroxides and unsaturated aldehydes are formed chemically by means of intermediates which in some cases are free radicals. Similar undesired processes take place in the ageing of substances which consist of relative long carbon chains, for example rubber, plastics and mineral oil. As is known, for example, the lipid-soluble BHA (butylated hydroryanisole, cf. Merck-Index, tenth edition, Rahway, U.S.A., 1983 No. 1521 page 215), the still better lipid-soluble BHT (butylated hydroxy-toluene, ibid, No. 1520), and the likewise lipid-soluble, but unstable, temperature- and light-sensitive vitamin E (ibid, No. 9832, page 1437) and the lipid-insoluble ascorbic acid (ibid, No. 846 page 120) are used as preservatives.

The present invention relates to novel antioxidants having particularly advantageous effects in lipophilic medium. They are compounds of the formula I

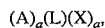  (I)

in which a, a', A, L and X have the following meaning:

a and a'=independently of one another the numbers 1 or 2,

A=an antioxidative component from the group comprising $A_1$—a chroman partial structure of vitamin E

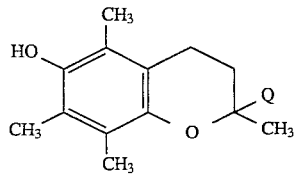

in which Q in this and all following formulae represents a free valency (covalent single bond), $A_2$—an alkyl-substituted mono-, di- or tri-phenol radical

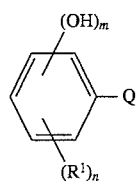

in which m=1 or 2, n=1 or 2, and m+n=3 or 4, $R^1$=an alkyl radical and/or an alkoxy radical and the total number of carbon atoms of the alkyl or alkoxy radical or the alkyl and alkoxy radicals is a maximum of 8;

$A_3$—a reductone radical

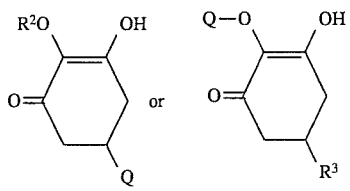

in which $R^2$=H or a lower alkyl radical (preferably $C_1$–$C_4$) and $R^3$=H, $COOR^4$ or $CH_2OR^4$ $R^4$=H or a lower alkyl radical (preferably $C_1$–$C_4$)

$A_4$—a 1,2-dithiacycloalkyl or 1,2-dithiacycloalkenyl radical having 2–6, preferably 2–4 carbon atoms in the ring and the dithiol form of these radicals which has been reduced by hydrogenation $A_5$—an ascorbic acid (derivative) radical

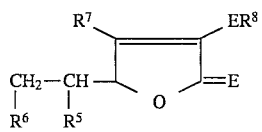

in which

E=O, S or $NR^9$ $R^5$=H, EH, EQ or Q $R^6$=H, EH, EQ—(L—$X_1$) or Q—(L—$X_1$)

$R^7$=H, EH, EQ, Q or one of the radicals mentioned under $A_2$ and $A_3$, $R^8$=H, EH, Q—(L—$X_1$) or —$PO(OR^9)_2$, $R^9$=H, a lower alkyl radical (preferably $C_1$–$C_4$) or Q, and only 1 or 2—preferably 1—of the radicals $R^5$–$R^9$ are identical to Q or contain Q, L=a bridging member and $X_1$=a lipophilic component as defined below;

L=a bridging member, composed of one or more of the building blocks

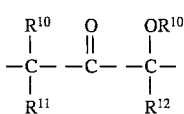

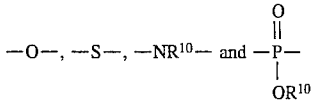

in which $R^{10}$, $R^{11}$, $R^{12}$=H, a lower alkyl radical (preferably $C_1$–$C_4$) or Q, $R^{11}$ can moreover also be —$CO_aR^{10}$ (where a=1 or 2), and 2 radicals of the type —O—, —S— and/or —$NR^{10}$— are separated from one another by at least 1 carbon or phosphorus atom;

X=a lipophilic component from the group comprising
X₁—cholane derivative radicals

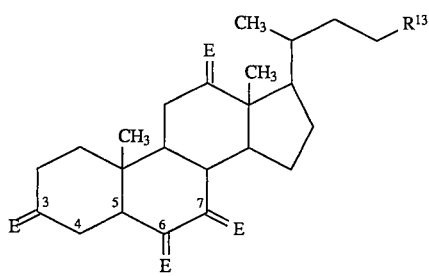

in which

R¹³=sec. C₄H₉ (=cholestane), R¹¹ (see under L) or Q,

E=O, S, NR¹⁰ (R¹⁰ see under L), (α,β-OH,H) or (α,β-Q, H) and a double bond can be present in the 4,5- or 5,6- or 7,8-position, and X₂—an alkyl or cycloalkyl radical or a fatty acid derivative radical having up to 24 carbon atoms.

Among the components A, L and X, the following radicals are preferred:

for A₄:

a radical of the following formulae in the dithia form (as in the formulae) or in the dithiol form which has been reduced by hydrogenation:

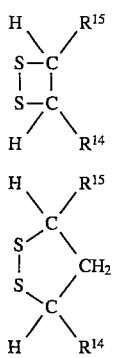   A₄.₁

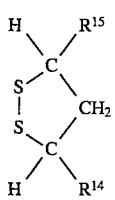   A₄.₂ in which

R¹⁴=H or a lower alkyl radical (preferably C₁-C₄), and
R¹⁵=—(CH₂)$_b$—Q
b=0–12, preferably 0–4.

In the case A₄.₂, particularly preferably:
R¹⁴=H and
R¹⁵=—(CH₂)₄—Q (=decarboxylipoic acid or -dihydrolipoic acid partial structure).

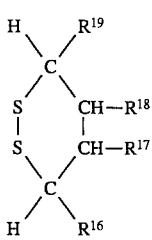   A₄.₃ in which

R¹⁸ and R¹⁹=independently of one another=H or a lower alkyl radical (preferably C₁-C₄)
R¹⁷=Q and R¹⁸=H, a lower alkyl radical (preferably C₁-C₄), an acyl radical OCOR¹⁸ or OR¹⁹

R¹⁹=a lower alkyl radical (preferably C₁-C₄) or Q.

A₄.₄ a dithiothreitol or dithioerythritol partial structure

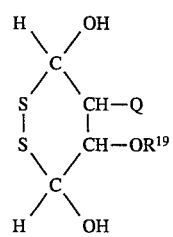

in which

R¹⁹ has the same meaning as in 4.3.

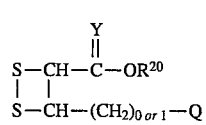   A₄.₅ in which

R²⁰=H or a lower alkyl radical (preferably C₁-C₄) and
Y=H₂ or O.

For A₅:

E=O

R⁵, R⁶ and R⁷=independently of one another=OH or OQ,
R⁸=H or Q, where only 1 or 2 radicals R⁵-R⁸ contain Q or are identical to Q (=an ascorbic acid radical).

Other particularly preferred radicals A are:

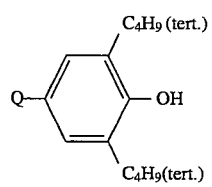

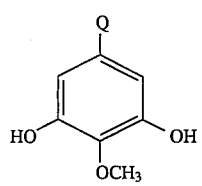

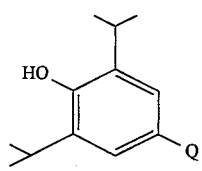

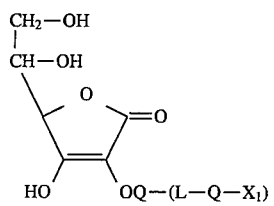

-continued

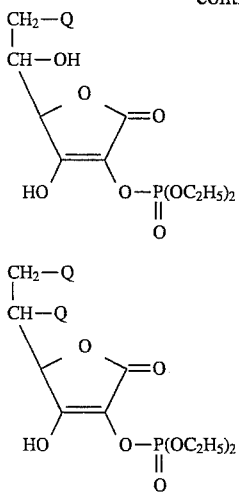

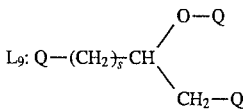

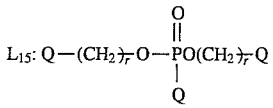

With respect to the antioxidative effect, L is an inert, chemically stable bridging member for linking A and X. Bridging members L which contain an ester bond are somewhat more sensitive to hydrolysis than bridging members without an ester component. This has to be taken into consideration if the stabilizing lipids come into contact with acids or alkalis. For example, in the case of use as pharmaceuticals, the cleavage of the ester bond by enzymes at the pharmacological site of action may, however, also offer advantages in that the antioxidative component is removed and concentrated exactly at the site of action.

L preferably has the following formula:

$$L = M_p\{[-(CH_2)_w-(G_1)_z-(G_2)]_v-(CH_2)_y-(G_3)_z-(G_4)_{p+1}\}M_p$$

in which p, x and z independently of one another=0 or 1, v, w and y independently of one another=0–4, and v+w+y+z=0–10, $M = -CR^{10}=$,

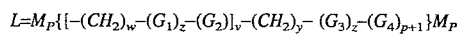

$G_1$, $G_2$, $G_3$ and $G_4$ independently of one another= —O—, —S—, —NR$^{10}$—,

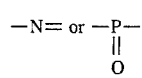

—CHOR$^{10}$— or —CH(CH$_2$—OR$^{10}$)—, where R$^{10}$ has the abovementioned meaning (=H, a lower alkyl radical or Q) and 2 of the radicals —O—, —S— and/or —NR$^{10}$— are separated from one another by at least 1 carbon atom.

L is particularly preferably a radical from the group comprising:

$L_1$: Q—O—(CH$_2$)$_r$—O—CO—Q $L_2$: Q—CO—NH—(CH$_2$)$_q$—NH—CO—Q $L_3$: Q—O—(CH$_2$—)$_r$—NH—CO—Q $L_4$: Q—(CH$_2$—)$_r$(—O—)$_b$—Q $L_5$: Q—(CH$_2$—)$_s$—O—(CH$_2$—)$_r$—O—Q $L_6$: Q—(CH$_2$—)$_s$—NH—(CH$_2$—)$_r$—O—Q $L_7$: Q—CO—NH—(CH$_2$—CH$_2$)$_r$—O—Q $L_8$: Q—O—(CH$_2$—)$_s$—CHOH—(CH$_2$—)$_s$—O—(CH$_2$—)$_s$—Q

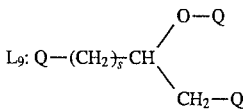

$L_{10}$: Q—(CH$_2$—)$_q$—Q $L_{11}$: Q—(CH$_2$—)$_s$—CHCO$_2$R$^{10}$—CHOH—Q $L_{12}$: Q—CH=C(CO$_2$R$^{10}$)—CO—Q $L_{13}$: Q—CO—NH—(CH$_2$—)$_q$—NH—CO—Q $L_{14}$: Q—(CH$_2$—)$_s$—O—(CH$_2$—)$_r$—O—

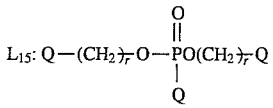

$L_{16}$: [Q—(CH$_2$—)$_2$—O—(CH$_2$)$_s$]$_2$CH—Q $L_{17}$: Q—O—(CH$_2$—)$_s$—CHOH—O—(CH$_2$—)$_s$—Q $L_{18}$: Q—O—(CH$_2$—)$_s$—CH(CH$_2$—OH)—O—CO—Q $L_{19}$: Q—O—(CH$_2$—)$_s$—CHOH—(CH$_2$—)$_s$—O—CO—O $L_{20}$: Q—CO—NR$^{10}$—Q $L_{21}$: Q—CO(O)$_x$—Q $L_{22}$: Q—CH$_2$—N[CH(CH$_3$)$_2$]—(CH$_2$)$_r$—CHOHCH$_2$CHOHCH$_2$—CO(O)$_x$—Q $L_{23}$: Q—(CH$_2$)$_s$—Q $L_{24}$: Q—NR$^{10}$—Q $L_{25}$: Q—O—Q $L_{26}$: Q—(CH$_2$)$_s$—CHCO$_2$R$^{10}$—COQ

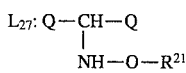

in which R$^{21}$=benzyl or R$^{10}$

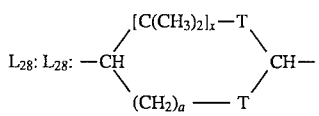

in which

T=O or S x=0 or 1 a=1 or 2;

q=1–5, preferably 3 r=1–5, preferably 2 s=1–5, preferably 1, and R$^{10}$ has the abovementioned meaning (=H, a lower alkyl radical or Q).

Very particularly preferred bridging members L are:

Q—CO—O—Q
Q—CO—NH—Q
Q—CO—NH—CH$_2$—CH$_2$—O—Q

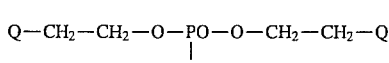

Q—CO—NH—(CH$_2$)$_3$—NH—CO—Q

-continued $$Q-O-CH_2-CH_2-O-CH_2-\underset{Q}{CH}-CH_2-O-CH_2-CH_2-O-Q$$

$$Q-CO-Q$$
$$Q-CO-NH-(CH_2)_3-NH-CO-Q$$
$$Q-CH_2-O-CH_2-CH_2-O-Q$$

$$Q-\underset{NH-O-CH_2-C_6H_5}{CH}-Q$$

$$Q-CH=\underset{COQ}{C}-CO_2C_2H_5$$

$$Q-CH_2-\underset{\underset{OH}{HC-Q}}{CH}-CO_2Na$$

Q—CH₂—CH
      /   \
     C     C—Q
     |     |
     O     O
      \   /
       X
      /   \
    CH₃   CH₃

Q—CH₂—CH
      /   \
     CH    CH—Q
     |     |
     OH    OH $$Q-CH_2-\underset{CO_2C_2H_5}{CH}-CHOH-Q$$

$$Q-CH_2-\underset{CO_2C_2H_5}{CH}-CO-Q$$

$$Q-COO-CH_2-CHOH-CH_2-O-Q$$

$$Q-COO-\underset{CH_2OH}{CH}-CH-O-Q$$

$$Q-CH_2-O-CH_2-CHOH-CH_2-O-Q$$

Q—CH
   / S—CH₂ \
  <         > CH—Q
   \ S—CH₂ /

$$Q-S-CH_2-CH_2-\underset{S-CH_2-Q}{CH}-(CH_2)_4CO_2\text{-tert.-butyl.}$$

X is preferably a radical from the following group:
$X_{1.1}$ cholesterol
$X_{1.2}$ cholestanol
$X_{1.3}$ cholic acid
$X_{1.4}$ desoxycholic acid
$X_{1.5}$ ursodesoxycholic acid
$X_{1.6}$ chenodesoxycholic acid and
$X_{2.1}$ $CH_3-(CH_2)_t-Q$
$X_{2.2}$ $Q-C(CH_3)_3$
$X_{2.3}$ $Q-CH(CH_2)_d$
$X_{2.4}$ $Q-C=C-(CH_2)_5-CH_3$
$X_{2.5}$ $R^{10}-CO_2-(CH_2)_z-Q$
d=4–6
t=3–24, preferably 6–18,
z=0 or 1

Particularly preferred radicals $X_1$ are:

[steroid structure with OH, CH₃, Q substituents]

[steroid structure with CH₃, Q substituents]

and particularly preferred radicals $X_2$ are:
$CH_3-(CH_2)_{16}-Q$
$CH_3-(CH_2)_{17}-Q$
$CH_3-(CH_2)_{18}-Q$
$CH_3-C(CH_2)_2-Q$
$CH_3-(CH_2)_5-C=C-Q$.

Preparation of the compounds of the formula I:

The compounds are prepared by processes which are generally known. The individual components A and X are employed free or protected, if appropriate in the form of reactive derivatives. Linking to L is carried out by means of a reactive derivative of L. In the case of the protected compounds, the protecting groups are removed again after the linking.

The process is represented more explicitly as described in the experimental section.

The compounds of the formula I according to the invention can be used as antioxidants, for example, in the fat-, oil-, plastics- and rubber-processing industry (such as the foodstuffs, cosmetics, pharmaceuticals, rubber and mineral oil industry), as preservatives for fatty substances (lipids) or for polymeric long-chain carbon compounds.

As explained below, the in vivo oxidation of lipid components (for example of blood fats or of lipids of the biomembranes) of the human or animal body also has undesired consequences: important lipids, in particular cholesterol, are transported in the blood with the aid of low density lipoprotein (LDL). Under physiological conditions, the LDL interacts with the blood vessel system in a controlled manner. It is absorbed into the vessel wall via specific receptors in a regulated process and there makes its lipid components available as energy carriers or as cell building blocks. If an insufficient antioxidative protective action is then present, for example in particular under hyperlipidemic conditions, oxidation of the blood lipids can occur. The oxidized blood lipids, or LDL, are then absorbed from the vessel walls unhindered while avoiding the specific LDL receptors, i.e. the controlled process of receptor regulation breaks down. In the course of these toxic processes, in which radical intermediates are involved in particular, oxidation products of cholesterol having mutagenic and cell-toxic properties, for example, are formed (Proc. Natl. Acad. Sci. U.S.A. 81 (1984) 4198–4202), while the unsaturated fatty acid radicals are oxidatively degraded to, for example, hydroxyalkenals having strong biocidal effects. In the further course of the disease, the vessel regions attacked are considerably damaged by so called foam cell formation with the participation of macrophages. Proliferation of the smooth vessel musculature occurs and finally the formation of atherosclerotic plaques which constrict the blood vessel. Blood clots can collect there and finally an infarct can lead to permanent damage or to the death of the patient. These pathological processes cannot be completely prevented alone by dietetic measures for the reduction of the blood lipid level. The medicinal reduction of the blood lipid level is indeed prior art, but has the disadvantage that it intervenes in the complex lipid metabolic processes. Under physiological conditions, these metabolic processes are in an exactly balanced equilibrium. An influence on this equilibrium, in particular over a relatively long period, will inevitably also lead to undesired biological reactions. Undesired side effects of lipid-reducing medicaments, such as clofibrate or nicotinic acid, are listed, for example, in Meyler's Side Effects of Drugs, 10th edition, 1984, Elsevier Amsterdam—New York— Oxford.

Because of their protective action which is compartmentalized in the lipids, the lipid-soluble antioxidants according to the invention are advantageously suited for the prevention and treatment of disorders in which (for example free radical) oxidation processes in the lipid medium play a role, in particular for the prevention and treatment of the processes described in disorders of the vessel wall. Owing to their particular antioxidative properties, the substances according to the invention can also be used in other medical problems in which bio-radicals are involved. These include, for example, inflammatory processes, in particular chronic inflammations such as rheumatism or arthritis, defective circulation as a result of, for example, cerebral damage, such as stroke, and death of nerve cells (Alzheimer's disease), peripheral vascular diseases, such as thromboses and atherosclerosis, but also undesired mutagenic, cell-toxic and carcinogenic effects as a result of light or radiation or as a result of chemicals, for example cancer therapeutics, such as adriamycin, as well as reperfusion damage, which can occur after opening vascular occlusions, but also after organ and tissue transplants, or after overcoming hypoxic conditions, for example in neonatal medicine. In addition, the compounds according to the invention are also suitable for curing liver damage.

For clinical therapeutic use, the antioxidants according to the invention can also be present in the form of prodrugs, for example in the form of their salts, from which the active compound is only formed in vivo. Metal cations which can be used are, for example, those of the alkali metals such as lithium, sodium and potassium, and of the alkaline earth metals such as magnesium and calcium, but also cationic forms whose metals, such as aluminum, zinc and iron are optionally chelated with citric acid or ethylenediaminetetraacetic acid and the like. Amine cations are those of primary, secondary or tertiary &mines such as the alkyl&mines, for example mono-, di- and trimethyl; or -ethyl-, -propyl-, -isopropyl-, -butyl-, -isobutyl-, -t-butyl-, and N-(methylhexyl)-, benzyl-β-phenylethylamine, ethylenediamine, diethylenetriamine, pyrrrolidine, piperidine, morphaline, piperazine, mona-, di- and trierhanolamine, ethyldiethanolamine, N-butylethanolamine, tris(hydroxymethyl)aminomethane and the like. Suitable amine salts are, for example, those of tryptamine, cysteine and the basic amine salts of lyeins and arginine. Suitable quaternary ammonium cations are, for example, tetramethylammonium and benzyltrimethylammonium. These cations can also be used for salt formation of the anionic forms of the compounds according to the invention, while chloride and fluoride are preferred for salt formation with the cationic forms.

Preparation of Antioxidative Compositions and of Pharmaceuticals

The compounds according to the invention are added to the lipids robe protected in a customary manner. The amount of the antioxidant according to the invention added can vary within wide ranges. As is explained in the experimental section, highly concentrated antioxidant/lipid solutions can in particular be prepared. Stabilized preparations of this type can then be processed in a large number of ways, for example in air, and then diluted again. After dilution, elastomers, rubber, plastics, fat and oils in general contain up to 1 percent by weight or more of the antioxidants described above, although an addition of 0.1% may be sufficient. For fats and oils which are used for human nutrition, 0.5 percent by weight, preferably 0.005–0.03percent by weight of the antioxidant according to the invention is used. Said mixture ratios can also be used for the production of liposomes. For use as pharmaceuticals for the prophylaxis and for the treatment of hyperlipidemic and thrombotic peripheral and cerebral diseases, in particular vascular diseases in humans and animals, the dosage necessary depends on the nature and severity of the disease, or on the animal species to be treated, but also on the age, weight and state of health of the patient. For humans, a dosage of 0.05 mg or 1 mg to 100 mg/day, in particular for intramuscular and intravenous dosage, may already be sufficient, the use of up to 200 mg or 500 mg/day, however, leading to a higher potency. Oral, peroral, rectal or (trans)dermal administration which, however, may make substantially higher dosages up to over 2.5 g/day necessary, although as a rule 50 mg to 800 mg/day are sufficient, is particularly simple. Said dosages can be administered either as a single dose per day, but also twice or three times to eight times daily in correspondingly reduced dose units.

The pharmaceutical preparations for said administrations are prepared according to the prior arc. The active compounds according to the invention can be present as a powder, gel, emulsion, dispersion or solution and are divided into portions, for example dropwise or by the spoonful, or as the contents of capsules (including microcapsules and liposomes), it being possible, however, when using capsules or liposomes for the shell also to assume the function of the active compound carrier. Dose units in the form of solid pharmaceutical forms, such as tablets (including coated tablets and pills), or suppositories can be prepared by customary methods such as pressing, dipping or fluidized bed methods, or pan coating and contain carriers and other customary auxiliaries, such as gelatine, agarose, starch, for example potato, corn or wheat starch, cellulose, such as ethyl cellulose, silica, various sugars, such as lactose, magnesium carbonate and/or calcium phosphates. The coating solution is usually composed of sugar and/or starch syrup and usually additionally contains gelatine, gum arabic, polyvinylpyrrolidone, synthetic cellulose esters, surface-active substances, plasticizers, pigments and similar additives corresponding to the prior art. Any customary flow-regulating agent, lubricant or glidant, such as magnesium stearate, and mold-release agents can be used for the production of the pharmaceutical forms. The active compounds, for example, can also be bound to ion exchangers (for example polystyrenedivinylbenzenesulfonic acid) or adsorbed on sustained release material or incorporated into the sustained release material (for example those based on cellulose or polystyrene resin, for example hydroxyethylcellulose). Sustained release of the active compounds can also be achieved by providing the layer concerned with customary gastric juice-insoluble coatings.

The outstanding antioxidative properties of the lipophilic compounds according to the invention are shown in the experimental section, in particular also in comparison to antioxidants according to the prior art.

PREPARATION EXAMPLES

The following compounds of the formula I were prepared; if in the individual compound formulae there is nothing or nothing else on the carbon atoms, the possible free valencies are saturated with hydrogen atoms:

1) N-<3-(6-Hydroxy-2,5,7,8-tetramethylchroman-2-carbamoyl)-propyl>cholic acid amide

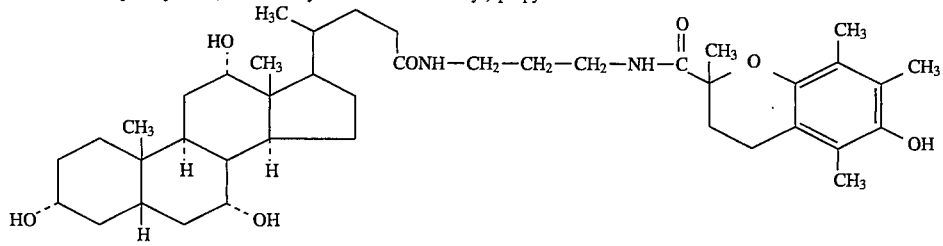

2) N-<3-(6-Hydroxy-2,5,7,8-tetramethylchroman-2-carbamoyl)-propyl>desoxycholic acid amide

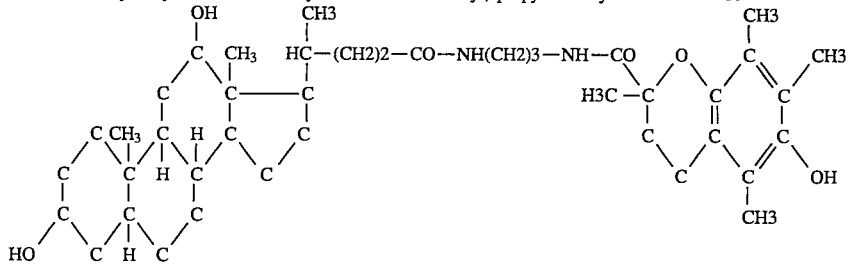

3) (30)-2-[N-(6-Hydroxy-2,5,7,8-tetramethylchroman-2-carbamoyl)aminoethyl]-3β,7α,12α-cholic acid

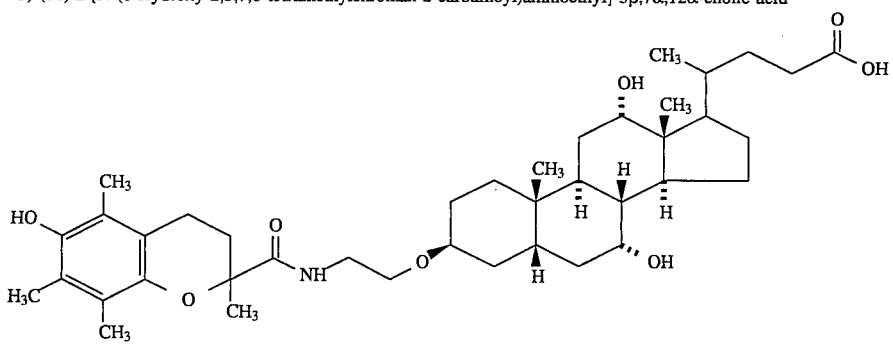

4) N-Hexyl-6-hydroxy-2,5,7,8-tetramethylchroman-2-carboxamide

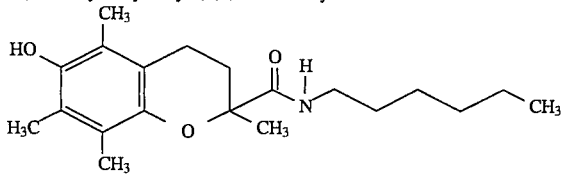

5) N-(3-Heptanamidopropyl)-6-hydroxy-2,5,7,8-tetra-methylchroman-2-carboxamide

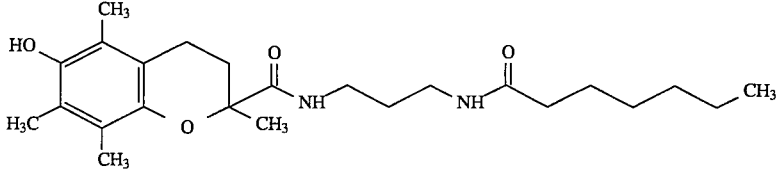

6) N-Octadecyl-6-hydroxy-2,5,7,8-tetramethylchroman-2-carboxamide

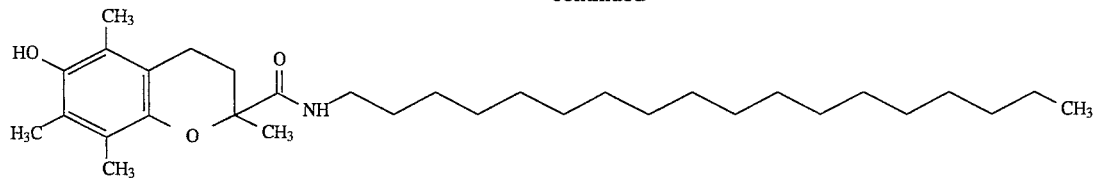

7) N-(3-Hexadecanamidopropyl)-6-hydroxy-2,5,7,8-tetra-methylchroman-2-carboxamide

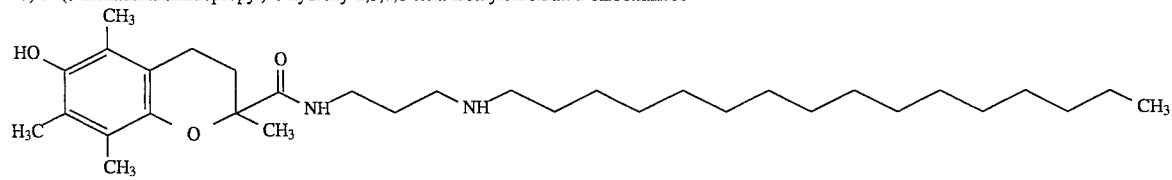

8) Cyclohexyl-6-hydroxy-2,5,7,8-tetramethylchroman-2-carboxamide

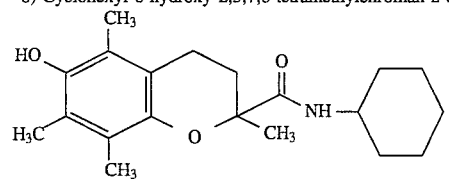

9) N-(3-Octadecanamidopropyl)-4-hydroxy-3-isopropyl-5-tert.-butylcarboxamide

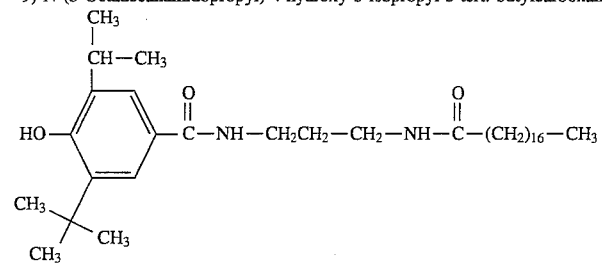

10) 4-[2-(5-Cholesten-3β-yloxy)-ethoxycarbonyl]-2,6-di-tert.-butylphenol

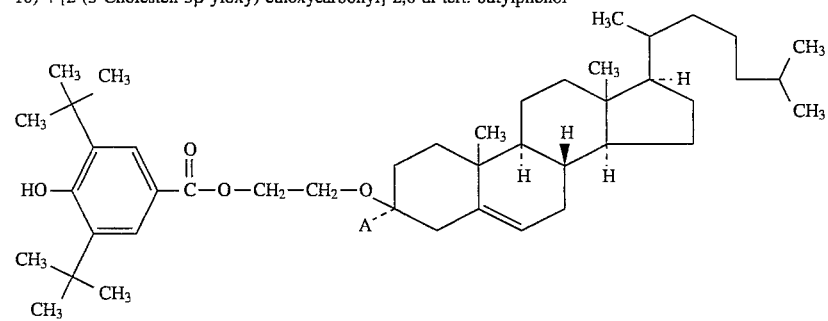

11) 3-[2-(5-Cholesten-3β-yloxy)ethoxycarbonyl]-1,5-dihydroxy-6-methoxyphenol

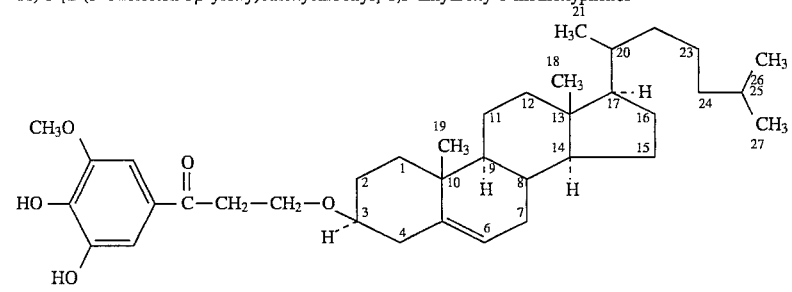

12) 4-[2-(5-Cholesten-3β-yloxy)-ethoxycarbonyl]-2,6-dihydroxy-1-methoxyphenol

-continued
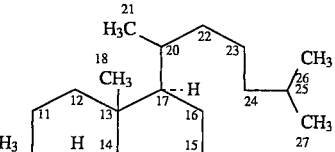
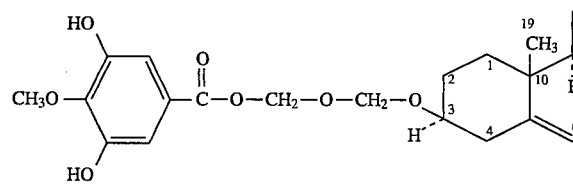
13) 4-<2-(5-Cholesten-3β-yloxy)-ethoxymethyl>-2,6-di-tert.-butylphenol
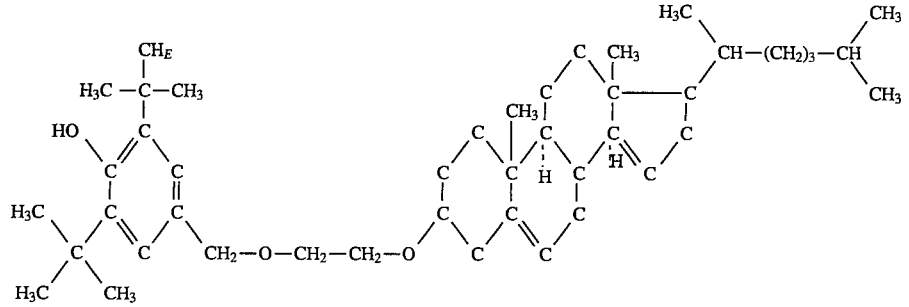
14) 4-[2-(Cholestan-3β-yloxy)-ethoxymethyl]-2,6-di-tert.-butylphenol
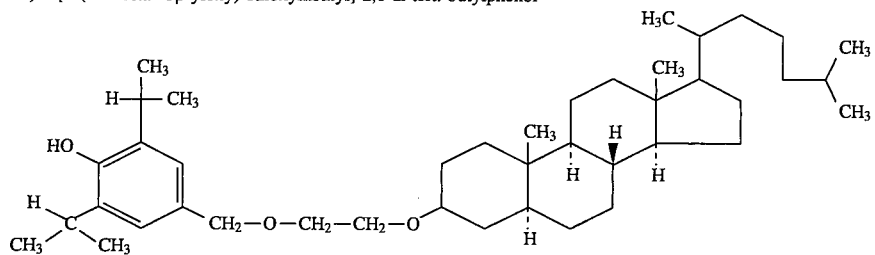
15) 4-[2-(Cholestan-3β-yloxy)-ethoxymethyl]-2-tert.-butyl-6-methylphenol
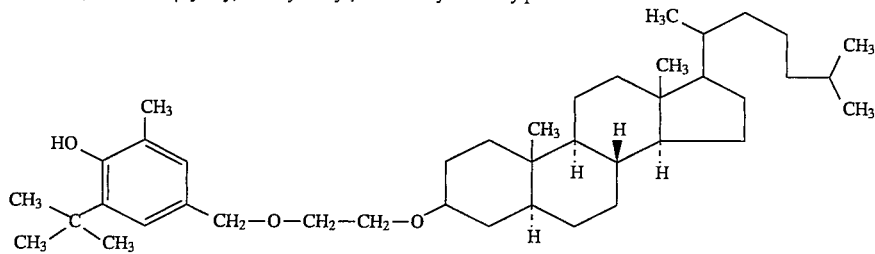
16) 4-[2-(7α,12α-Trihydroxy-5β-cholanic acid-3β-yloxy)-ethoxymethyl]-2,6-diisopropylphenol
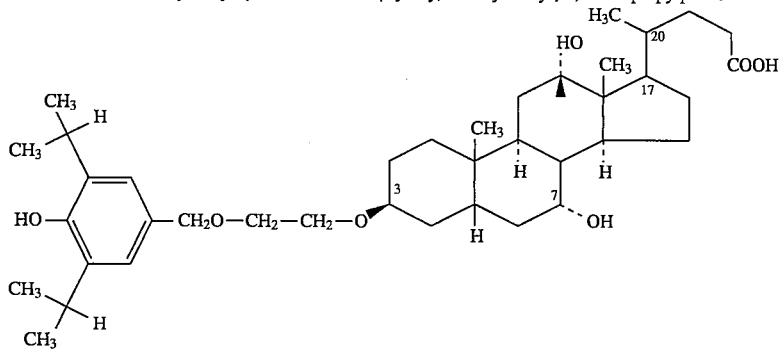
17) 2,6-Di-tert.-butyl-4-<7-nonynoyl>phenol

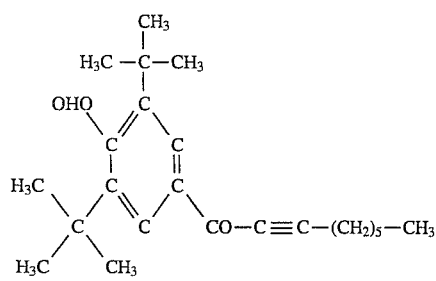
18) Ethyl 2-(3,5-di-tert.-butyl-4-hydroxybenzyl)-3-oxo-docosanoate
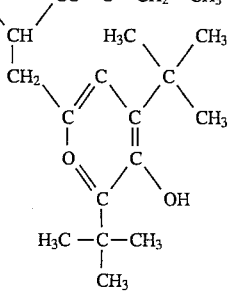
19) 5-[2-(3,5-Di-tert.-butyl-4-hydroxyphenyl)-1,3-dithian-4-yl]-valeric acid
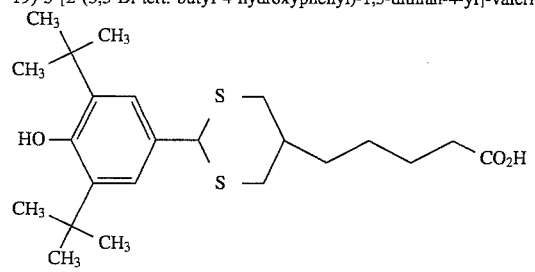
20) tert.-Butyl 6,8-bis((3,5-di-4-hydroxy-phenyl)-methyl-thio)octanoate
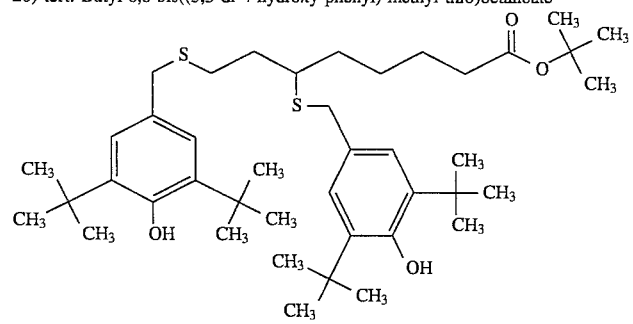
21) 2(R,S)-1-O-(3,5-Di-tert.-butyl-4-hydroxybenzyl)-3-O-octadecylglycerol
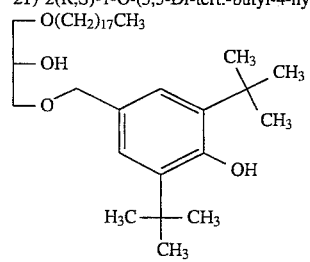
22) 2(R,S)-2-O-(3,5-Di-tert.-butyl-4-hydroxybenzoyl)-1-O-octadecylglycerol

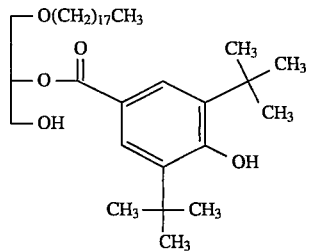
23) 2(R,S)-1-O-(3,5-Di-tert.-butyl-4-hydroxybenzoyl)-3-O-octadecylglycerol
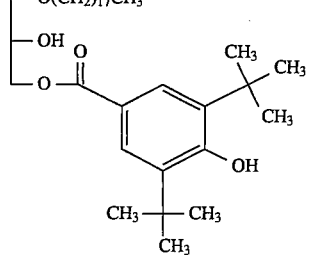
24) Ethyl 2-(3,5-di-tert.-butyl-4-hydroxybenzyl)-3-hydroxydocosanoate
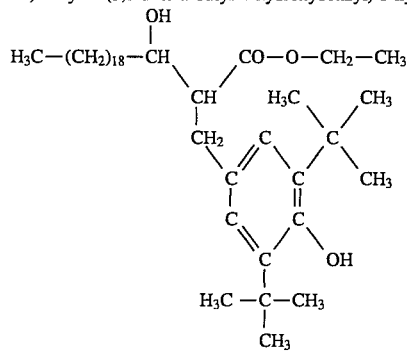
25) 1,3-Dihydroxy-2-(3,5-di-tert.-butyl-4-hydroxybenzyl)-docosane
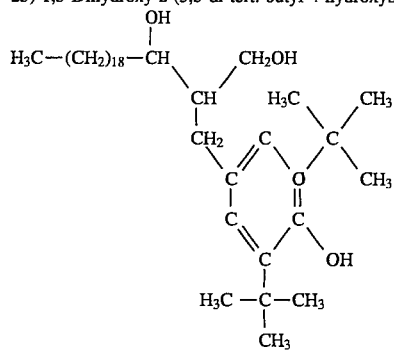
26) 5(R,S)-(3,5-Di-tert.-butyl-4-hydroxybenzyl)-2,2-dimethyl-6(R,S)-nonadecyl-1,3-dioxolane
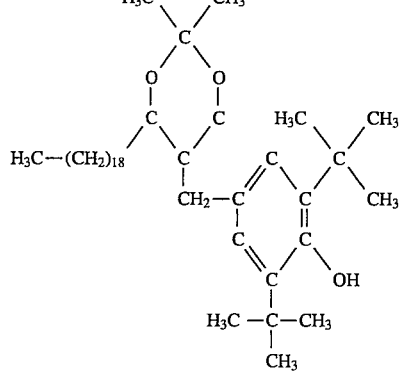

27) Ethyl 2-(3,5-di-tert.-butyl-4-hydroxybenzyl)-3-hydroxydocosanoate
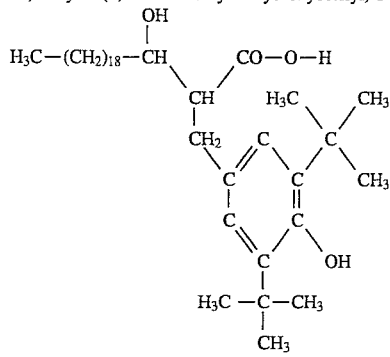
28) Ethyl (E,Z)-2-(3,5-di-tert.-butyl-4-hydroxybenzyl-idene)-3-oxodocosanoate
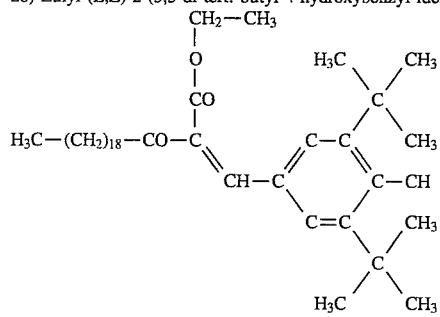
29) 2-O-Octadecyl-3-O-(3,5-di-tert.-butyl-4-hydroxy-phenylmethyl)ascorbic acid
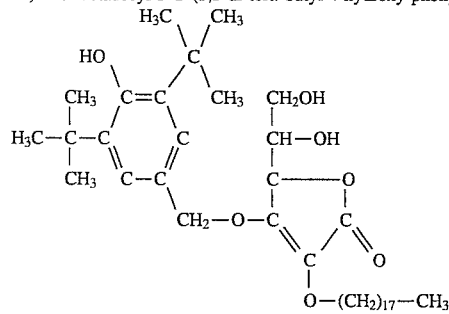
30) 2-Cholesteryloxyethyl 3'-keto-4',5'-dihydroxy-1',2',6'-trihydrobenzoate
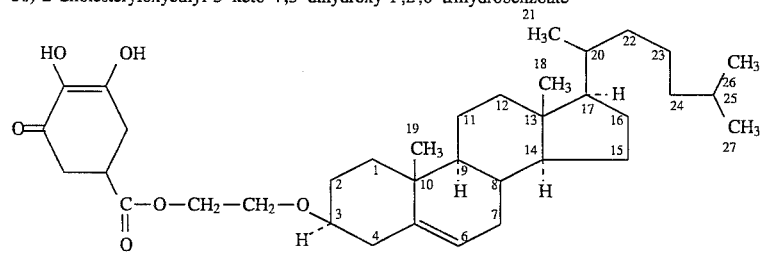
31) 4-Octadecoxy-5-hydroxy-3-keto-4,5-dehydrocyclo-hexanecarboxylic acid
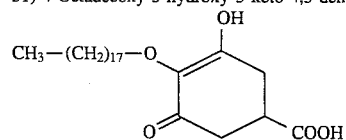
32) Octadecyl 3-keto-4,5-dihydroxy-1,2,6-tri-hydro-benzoate
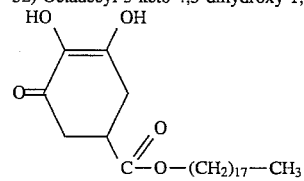

33) 2-O-(2-Cholesteryloxyethyl)ascorbic acid
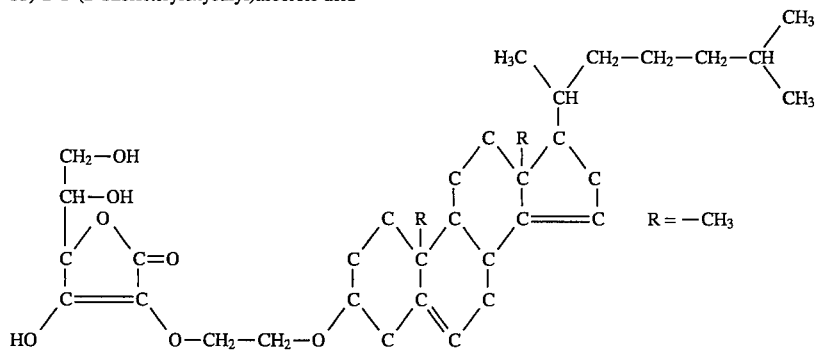
R = —CH$_3$
34) 6-O-Octadecanoyl-2-O-(O*,O*-diethylphosphoryl)-ascorbic acid
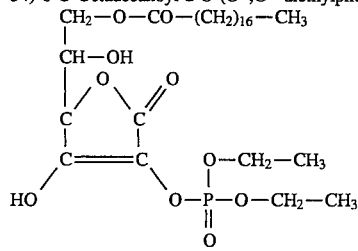
35) 5-O,6-O-Dioctadecanoyl-2-O-(O*,O*-diethylphosphoryl)-ascorbic acid
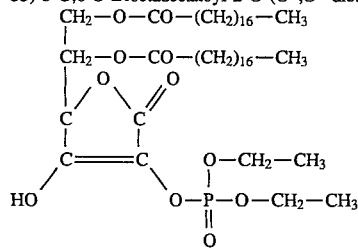
36) 1,3-Bis<2-(2-O-ascorbyloxy)ethoxy>-2-octadecylpropane
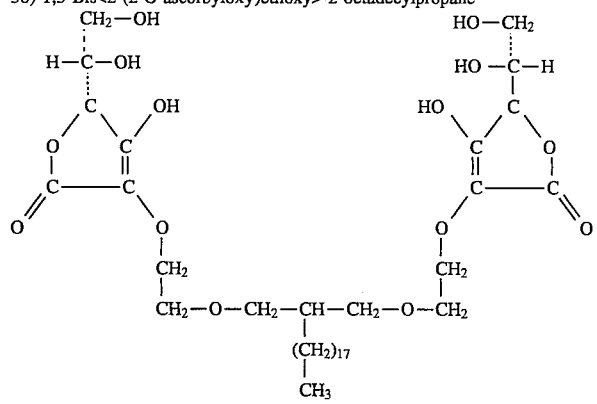
37) Di-(2-O-ascorbyl) octadecylphosphonate
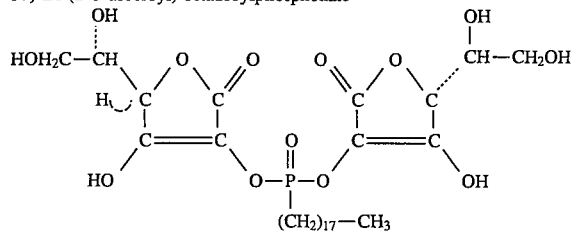
38) 4,5-Dithiacyclohexyl 1,2-distearate

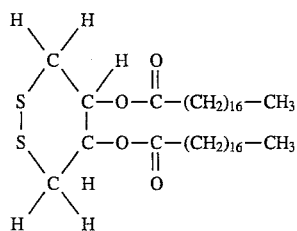
39) 4,5-Dithiacyclohexyl 1,2-disterate, reduced
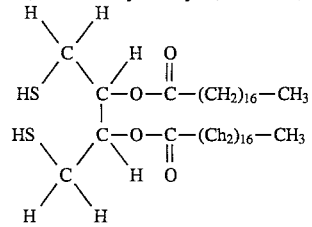
40) 4,5-Dithia-2-hydroxycyclohexyl stearate
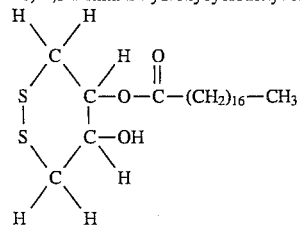
41) 4,5-Dithia-2-hydroxycyclohexyl stearate, reduced
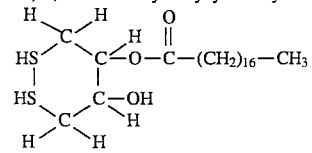
42) 2-Hydroxy-4,5-dithiacyclohexylursodesoxycholate
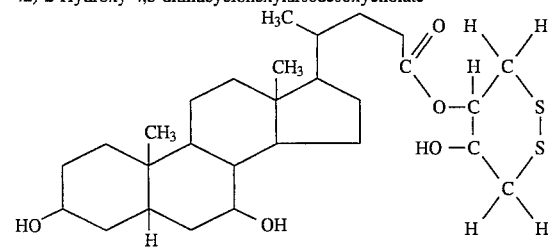
43) 2-Hydroxy-4,5-dithicyclohexyldesoxycholate, reduced
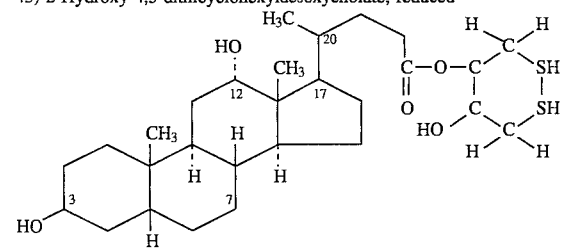
44) Bis(cholesteryl 6(R,S)-(2',3'-dimercaptosuccinate), oxidized

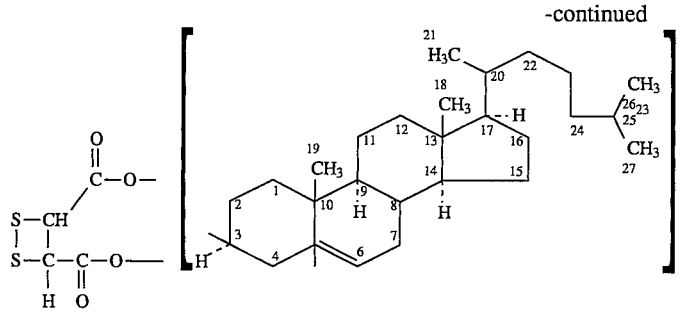
45) Cholesteryl 6(R,S)-(2',3'-dimercaptoethylsuccinate)
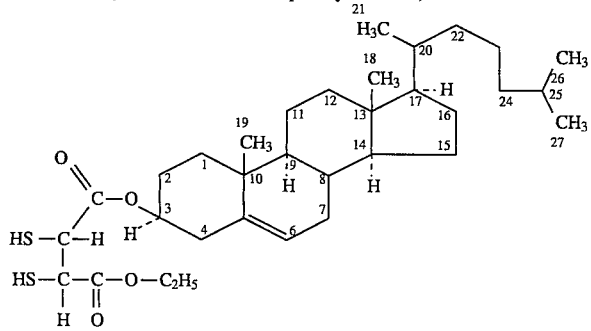
46) Cholesteryl 6(R,S)-dihydrolipoate
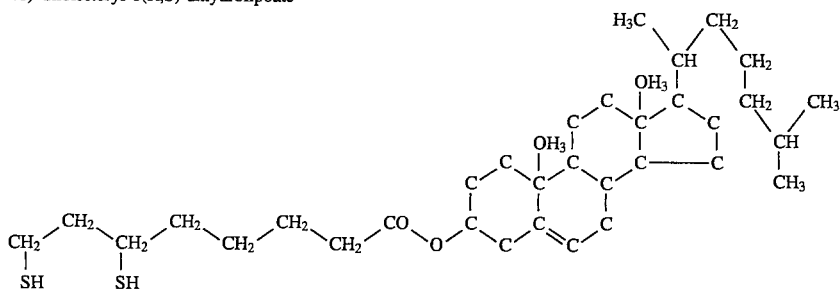
47) N-2-(5-Cholesten-3α-yloxy)ethyldihydrolipolic acid amide
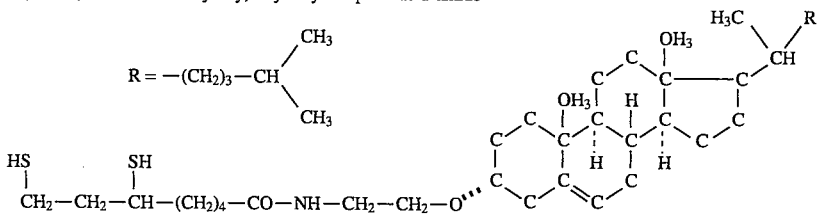
48) N-<3-(6,8-Dimercaptooctanoylamino)propyl>desoxycholic acid
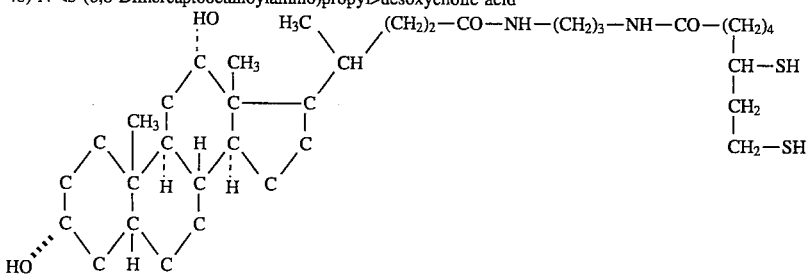
49) N-Octadecyl-DL-dihydrolipoic acid amide
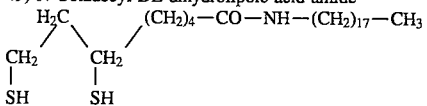
50) Octadecyl DL-dihydrolipoate

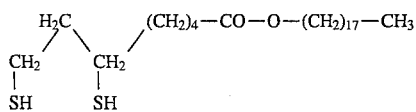

51) Octadecyl DL-α-lipoate

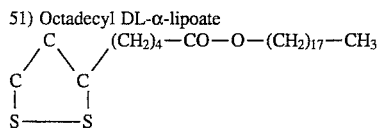

52) N-Octadecyl-DL-α-lipoic acid amide

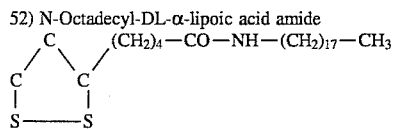

53) Cholesteryl 6(R,S)-lipoate

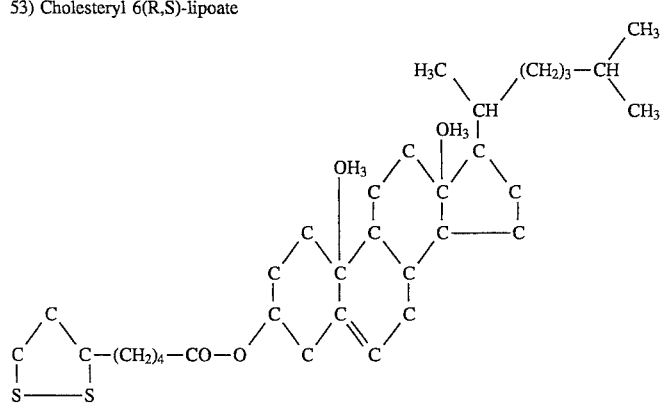

The preparation of these compounds is now described in the following; starting materials and intermediates are denoted by numbers from 70 upwards.

EXAMPLE 1

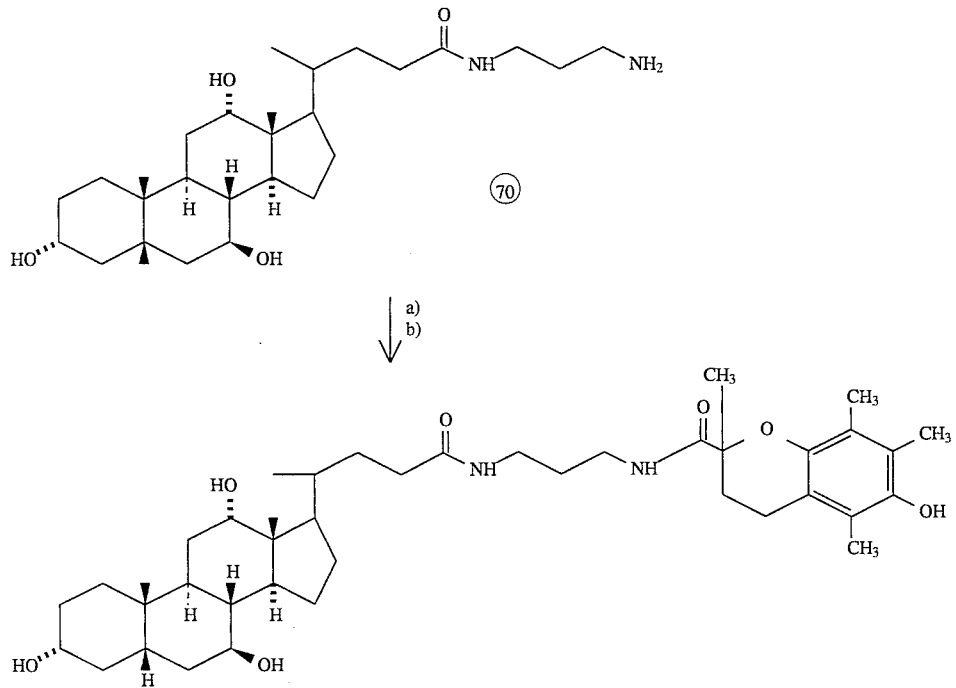

a) 1.0 g (4.0 mmol) of 6-hydroxy-2,5,7,8-tetramethyl chroman-2-carboxylic acid (Aldrich) was dissolved in 50 ml of THF/2.8 ml of triethylamine and 0.77 ml (8.0 mmol) of ethyl chloroformate was added at 0° C. The mixture was stirred at 0° C. for 15 min and at room temperature for 30 min. 1.86 g (4.0 mmol) of solid amine 70 [prepared by reaction of methyl chlorate with 1,3-diaminopropane (in excess without solvent), 5 h, reflux] were then added and the mixture was stirred at room temperature for 3 h. The reaction mixture was poured into water and extracted using ethyl acetate (3x), and the combined organic phases were dried (MgSO$_4$) and concentrated. Chromatography on silica gel (ethyl acetate/methanol= 10:1) gave 2.11 g of a white solid. m.p. 102°–105° C.

b) To liberate the phenol, 2.11 g (2.74 mmol) of the product obtained by a) were dissolved in 50 ml of methanol and 3.8 g (27 mmol) of potassium carbonate were added. The mixture was heated under reflux for 1 h and the solvent was largely evaporated. The residue was thoroughly stirred with water and the product was filtered off with suction. Chromatography on silica gel (CH$_2$Cl$_2$/MeOH=10:1.5 ) gave 1.5 g (79% ) of Example 2, m.p. 135°–140° C.

C$_{41}$H$_{64}$N$_2$O$_7$ (696), MS[1] (FAB[2]), 3-NBA[3]/LiI): 703 (M[4]+Li$^+$ Abbreviations familiar to the person skilled in the art:

[1] MS=Mass spectrum
[2] FAB=Fast atom bombardment
[3] 3-NBA=
[4] M$^+$=Molecular ion The examples in Table 1 were obtained completely analogously to Example 1.

TABLE 1

| Example | R | MS |
|---|---|---|
| 2 |  | C$_{41}$H$_{64}$N$_2$O$_6$ (608)<br>MS (FAB): 681 |
| 3 |  | C$_{40}$H$_{61}$NO$_8$ (683)<br>MS (FAB, 3'NBA/LiI): 696<br>(M + 2Li − H), 690<br>(M + Li) |
| 4 | —(CH$_2$)$_5$—CH$_3$ | C$_{20}$H$_{32}$NO$_3$ (333)<br>MS (DCI): 334<br>(M + H) |
| 5 | —(CH$_2$)$_3$NH—C(=O)—(CH$_2$)$_5$—CH$_3$ | C$_{24}$H$_{38}$N$_2$O$_4$ (418)<br>MS (FAB): 419 |
| 6 | —(CH$_2$)$_{17}$—CH$_3$ | C$_{32}$H$_{55}$O$_3$N (501)<br>MS (DCI): 502 |
| 7 | (CH$_2$)$_3$NH—C(=O)—(CH$_2$)$_{14}$—CH$_3$ | C$_{33}$H$_{56}$N$_2$O$_4$ (544)<br>MS (DCI): 545 |
| 8 | —C$_6$H$_{11}$ (cyclohexyl) | C$_{20}$H$_{29}$NO$_3$ (331)<br>MS (DCI): 332 |

EXAMPLE 13

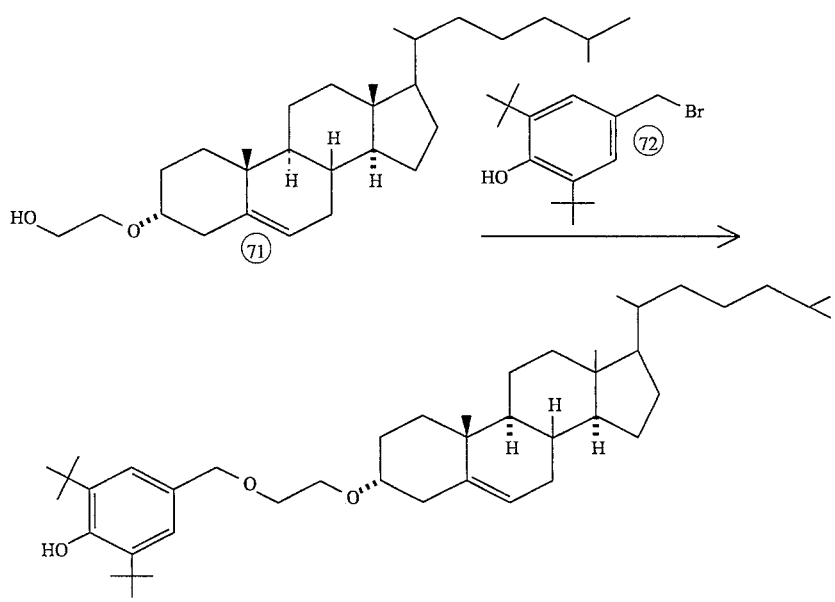

500 mg (1.16 mmol) of steroid alcohol ⑦₁ (J. Med. Chem. 1980, 1185) dissolved in a little THF were added dropwise to 61 mg (1.27 mmol) of sodium hydride in 5 ml of THF/5 ml of DMF. The mixture was then warmed to 50°–60° C. for 30 min. 180 mg (0.6 mmol) of solid bromide ⑦₂ were then added at 0° C. After 1 h at room temperature, a further 80 mg of bromide are added. The mixture was stirred at room temperature for a further 1 h and poured into water, and the aqueous phase was acidified using 1N HCl and extracted using ether (3x). The combined ether phases were washed with satd. NaHCO₃ solution and dried (MgSO₄). Evaporation and chromatography on silica gel (cyclohexane/ethyl acetate=9:1) gave 240 mg of Example 13 after crystallisation from methanol. m.p. 108°–110° C. $C_{44}H_{72}O_3$ (648), MS (FAB, 3-NBA/LiI): 655 (M+Li⁺)

The examples in Table 2 were obtained in analogy to Example 13 by alkylation of the appropriate alcohols (prepn. see below) with the bromide 72.

TABLE 2

| Example | R | MS |
|---|---|---|
| 21 | H₂C—O—(CH₂)₁₇—CH₃<br>    \|<br>HC—OH<br>    \|<br>H₂C— | $C_{36}H_{66}O_4$ (562)<br>MS (DCI): 563<br>(M + H⁺) |

Starting material: Helv. Chimica Acta 71, 274 (1988)

TABLE 2-continued

| Example | R | MS |
|---|---|---|
| 29 | OH, OH, (structure with O—(CH₃)₁₇—CH₃) | $C_{39}H_{65}O_7$ (645)<br>MS (DCI): 646<br>(M + H⁺) |

Starting material: cf. J. Med. Chem. 31, 793 (1988)

EXAMPLE 20

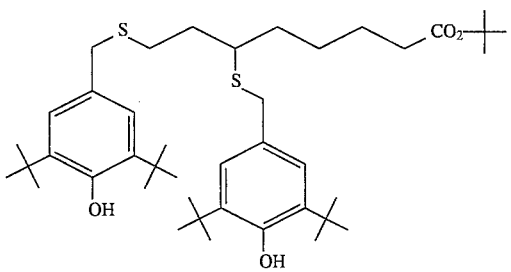

Example 20 was obtained from t-butyl dihydrolipoate and 2 equivalents of bromide 72 in the same manner. t-Butyl dihydrolipoate was obtained according to Examples 46–50 and t-butyl lipoate according to Examples 53 and 51. $C_{42}H_{68}S_2O_4$ (700), MS (DCI): 701 (M+H⁺)

EXAMPLE 17

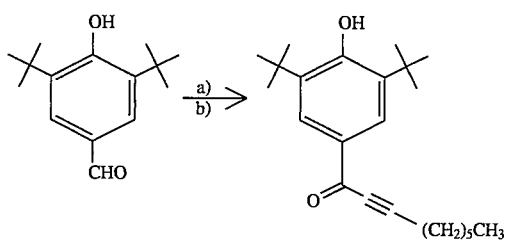

a) 21 ml (33.6 mmol) of n-BuLi (hexane) were added dropwise under an argon atmosphere between −20° C. and −40° C. to a solution of 5 ml (33.8 mmol) of n-octyne. After 1 h, 2.8 g (12 mmol) of 3,5-di-tert.-butyl-4-hydroxybenzaldehyde (Aldrich), dissolved in a little THF, were added dropwise. The mixture was stirred overnight at room temperature. The reaction mixture was poured into 2N HCl/ice and extracted using ether (3x). The combined organic phases were washed with saturated sodium hydrogen carbonate solution (2x) and dried (MgSO$_4$). Evaporation gave 4.96 g (quant.), which was further reacted according to b).

b) 4.96 g of the alcohol obtained according to a) were dissolved in 45 ml of dichloromethane and 4.66 g (21mmol) of pyridinium chlorochromate were added. After 2 h at room temperature, the mixture was diluted with ether and the solution was decanted. Filtration through silica gel (cyclohexane/ethyl acetate=3:1) gave 2.82 g (57%) of Example 17. m.p. 63°–65° C.

EXAMPLE 72

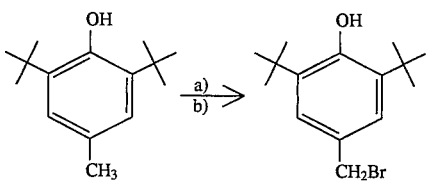

44.8 g (0.2 mol) of 2,6-di-tert.-butyl-p-cresol, 35.6 g (0.2 mol) of NBS and 400 mg of AIBN in 500 ml of carbon tetrachloride were heated under reflux for 2 h. After cooling, the mixture was filtered off and evaporated. Yield 63.9 g (quantitative) of Example 72.

EXAMPLE 18

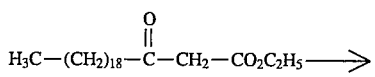

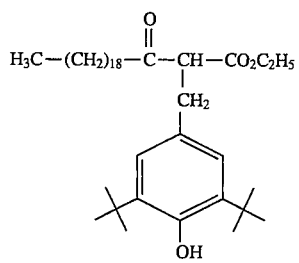

3.82 g (10 mmol) of keto ester 73 [keto ester 73 was obtained by dianion alkylation of ethyl aceto acetate with octadecyl iodide. NaH and buli were used as bases] in 15 ml of THF were added dropwise at 0° C. under nitrogen to 1.09 g (25 mmol) of sodium hydride in 5 ml of THF. The mixture was stirred at 0° C. for 30 min and 3.0 g (10 mmol) of bromide 72, dissolved in 10 ml of THF, were then added at this temperature. After 2 days at room temperature, the reaction mixture was poured into cold saturated ammonium chloride solution and extracted using ether (3x). The combined organic phases were dried (MgSO$_4$) and evaporated. Prep. HPLC (cyclohexane/ethyl acetate=12:1) gave 3.9 g (65%) of Example 18. C$_{39}$H$_{68}$O$_4$ (600), MS (DCI): 601 (M+H$^+$)

EXAMPLE 19

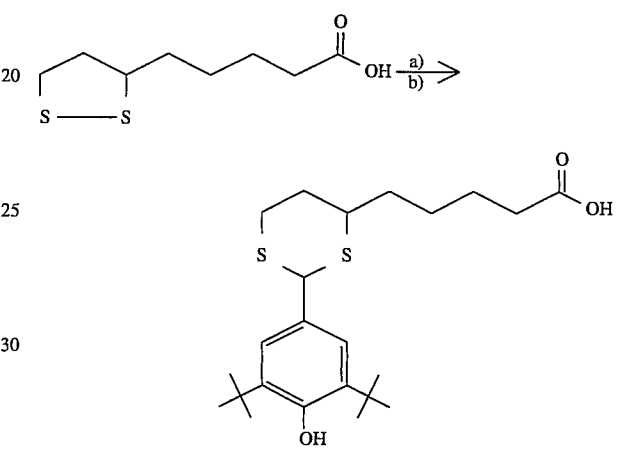

a) 100 mg (0.48 mmol) of DL-a-lipoic acid were dissolved in 2 ml of 0.25N aqueous sodium hydrogen carbonate solution and 20 mg of sodium borohydride were added. The mixture was stirred at 0° C. for 30 min, 2 ml of toluene were added and it was adjusted to pH 1 using 2N hydrochloric acid. The organic phase was separated off end evaporated.

b) The residue obtained according to a) was taken up in 5 ml of dichloromethane end 114 mg(0.48 mmol) of 3,5-di-tert.-butyl- 4-hydrorybenzaldehyde were added. 60 μl (0.48 mmol) of boron trifluoride etherate were then added and the mixture was stirred at room temperature for 1 h. The reaction mixture was partitioned between water and ethyl acetate. The organic phase was separated off, dried (MgSO$_4$) and evaporated. Chromatography on silica gel (cyclohexane/ethyl acetate=2:1) gave 135 mg (66%) of Example 19. m.p. 67°–68° C. C$_{23}$H$_{36}$O$_3$S$_2$ (424).

EXAMPLE 24

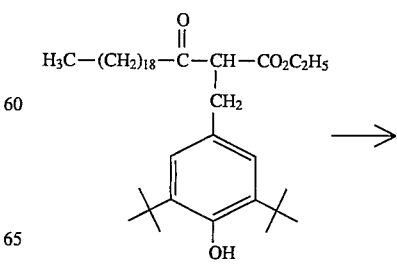

37
-continued

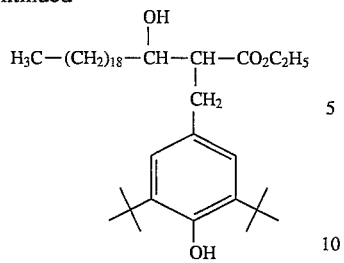

500 mg (0.83 mmol) of Example 18 were dissolved in 15 ml of ethanol and 112 mg (2.5 mmol) of sodium borohydride were added at 0° C. After stirring at 0° C. for 1.5 h, the reaction mixture was poured into 50 ml of cold, saturated ammonium chloride solution and extracted using ether (3x). The combined ether phases were dried (MgSO$_4$) and evaporated. Chromatography on silica gel (cyclohexane/ethyl acetate=4:1) gave 480 mg (95%) of Example 24. C$_{39}$H$_{70}$O$_4$ (602), MS (FAB, 3-NBA/LiI): 609 (M+Li$^+$)

EXAMPLE 25

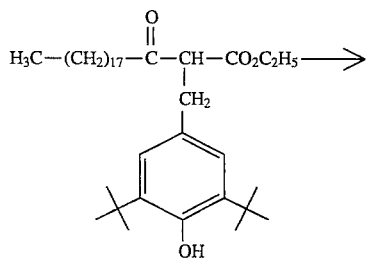

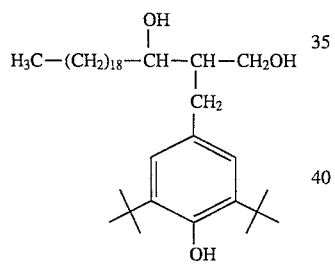

500 mg (0.83 mmol) of Example 18, dissolved in 5 ml of THF, were added dropwise at 0° C. under nitrogen to 65 mg (1.67 mmol) of lithium aluminum hydride in 10 ml of THF. The mixture was stirred at room temperature for 2 h. The reaction mixture was poured into saturated aqueous ammonium chloride solution and extracted using ether (3x). The combined ether phases were dried (MgSO$_4$) and evaporated. Chromatography on silica gel (cyclohexane/ ethyl acetate= 1:1) gave 460 mg of Example 25. m.p. 77°–78° C. C$_{37}$H$_{68}$O$_3$ (560), MS (FAB, 3-NBA/LiI): 567 (M+Li$^+$).

EXAMPLE 26

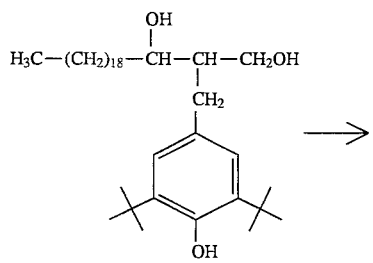

38
-continued

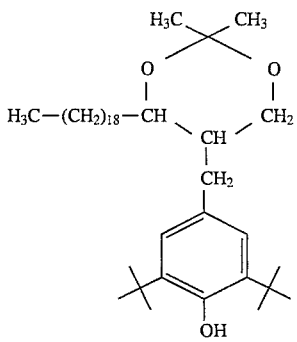

168 mg (0.3 mmol) of Example 25 were dissolved in 10 ml of acetone and 0.5 ml of acetyl chloride was added at room temperature. The mixture was stirred at room temperature for 1 h, ether was added and the solution was washed with saturated aqueous sodium hydrogen carbonate solution. Drying (MgSO$_4$), evaporation and chromatography of the residue on silica gel (cyclohexane/ethyl acetate =5:1) gave 164 mg (91%) of Example 26. C$_{40}$H$_{72}$O$_3$ (600), MS (DCI): 600 (M+).

EXAMPLE 27

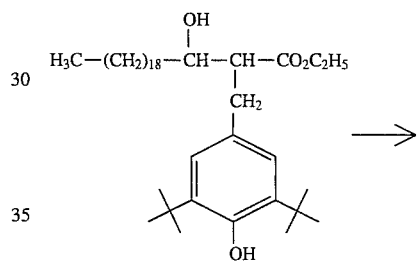

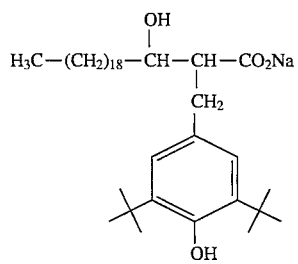

150 mg (0.25 mmol) of Example 24 were dissolved in 5 ml of ethanol and 5.0 ml of 0.1N sodium hydroxide solution were added. The mixture was heated under reflux for 8 h. The reaction mixture was poured onto ice/HCl and extracted using ether (3x). The combined organic phases were washed with saturated sodium chloride solution (1x) and dried. Evaporation gave the free acid. 131 mg of the free acid were dissolved in ethanol and 2.23 ml of 0.1N aqueous sodium hydroxide solution were added. The solution was evaporated several times with the addition of toluene. 130 mg of sodium salt of Example 27 were obtained.

EXAMPLE 28

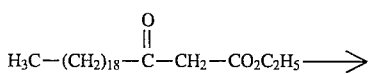

(73)

-continued

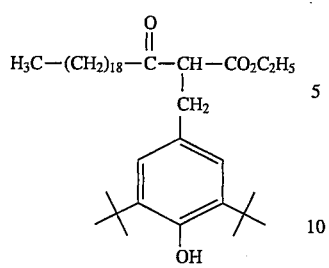

1.0 g (2.61 mmol) of keto ester 73, and 613 mg (2.61 mmol) of 3,5-di-tert.-butyl-4-hydrorybenzaldehyde (Aldrich) were heated under reflux for 3 days in 10 ml of pyridine with the addition of 93 μl (1.2 mmol) of glacial acetic acid and 10 μl (0.1 mmol) of piperidine. The mixture was diluted with toluene and washed with semi-saturated sodium chloride solution and dried ($Na_2SO_4$). Evaporation and chromatography on silica gel (cyclohexane/ethyl acetate=7:1) gave 740 mg (47%) of Example 28.

$C_{39}H_{66}O_4$ (598), MS (DCI): 599 ($M+H^+$)

EXAMPLE 33

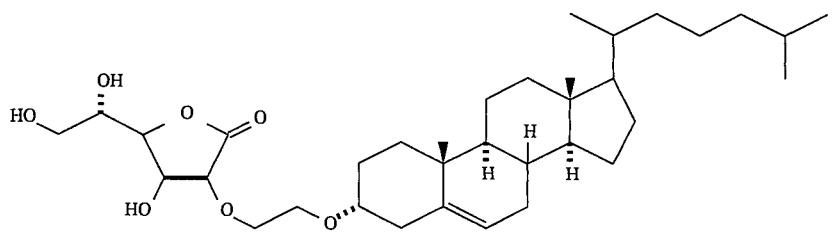

33 was prepared from Examples 74 and 71 in analogy to Examples 82, 75 (procedure b) and 34.

$C_{35}H_{56}O_7$ (588), MS (FAB): 601 (M+2Li-H), m.p.>160° (dec.)

EXAMPLE 75

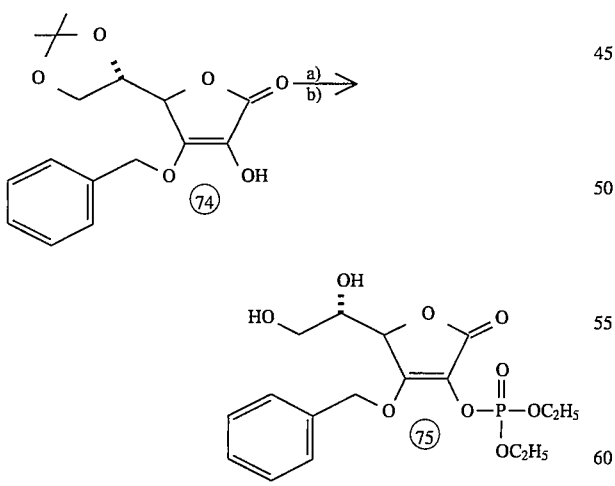

a) 44.9 g (0.146 mol) of alcohol 74 were dissolved in 300 ml of dichloromethane and 103 ml (0.733 mol) of triethylamine were added at 0° C. 23.2 ml (0.161 mol) of diethyl chlorophosphate were added dropwise at 0° C. and the mixture was stirred at 0° C. for 3 days. The reaction mixture was poured into saturated aqueous ammonium chloride solution and extracted using ether (3x). The combined organic phases were dried ($MgSO_4$) and evaporated. Chromatography on silica gel (cyclohexane/ethyl acetate =3:2) gave 18.1 g (28%). Rf (cyclohexane/ethyl acetate =1:1): 0.20.

b) To cleave the acetonide, the 18.1 g obtained according to a) dissolved in 50 ml of ethanol were added to 170 ml of ethanolic HCl [prepared by dropwise addition of 3.0 ml of acetyl chloride to 167 ml of ethanol] and the mixture was heated under reflux for 2 h. The solvent was evaporated and the residue was filtered through Florisil (ethyl acetate). After evaporating, 14.1 g (85%) of diol 75 were obtained. Rf (ethyl acetate): 0.33.

EXAMPLES 76 AND 77

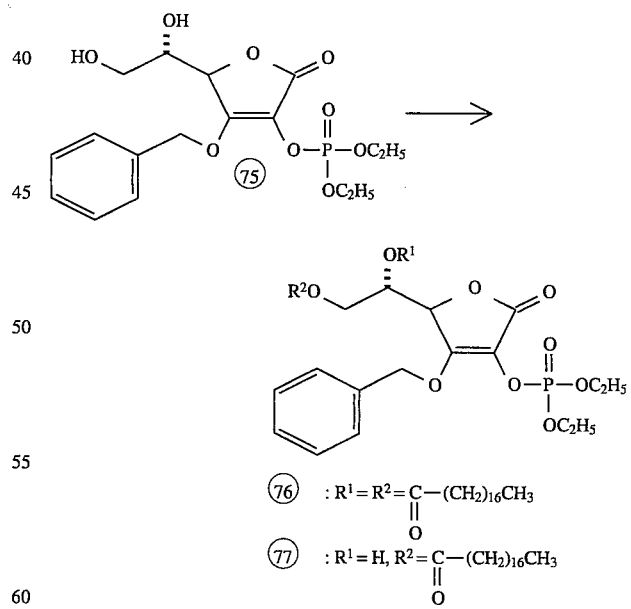

EXAMPLE 76

2.01 g (5 mmol) of diol 75 were dissolved in 20 ml of pyridine and 4.8 g (15 mmol) of stearoyl chloride were added at room temperature. The mixture was stirred for 30 min and poured into cold 2N hydrochloric acid, and the produce was filtered off with suction. Chromatography on silica gel (cyclohexane/ethyl acetate=7:3) gave 4.11 g (88%) of Example 76.

EXAMPLE 77

Example 77 was obtained completely analogously to 76 using one equivalent of stearic acid.

EXAMPLE 34

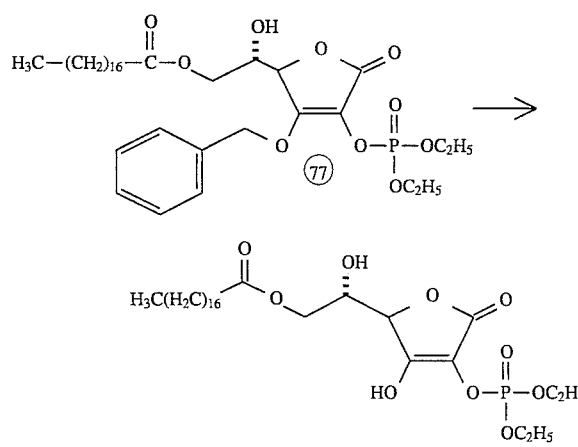

540 mg (0.81 mmol) of Example 77 in 10 ml of ethanol were hydrogenated at normal pressure and room temperature using 100 mg of Pd/C (10%). The catalyst was filtered off, the filtrate was evaporated and the residue was triturated with n-pentane. Yield 335 mg (71%) of Example 34. m.p. 84°–85° C.

$C_{28}H_{51}O_{10}P$ (578): MS (FAB, 3-NBA/LiI): 585 ($M+Li^+$), 591 (M+2Li-H).

EXAMPLE 35

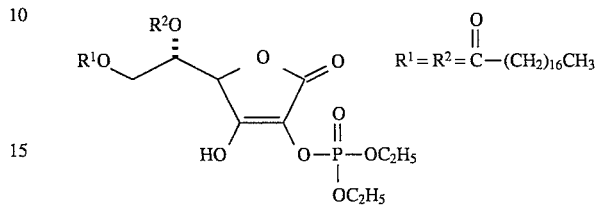

Example 35 was obtained completely analogously to Example 34.

m.p. 88°–90° C.

$C_{48}H_{85}O_{11}$ (845), MS (FAB, 3-NBA/LiI): 851 ($M+Li^+$), 857 (M+2Li-H).

EXAMPLE 78

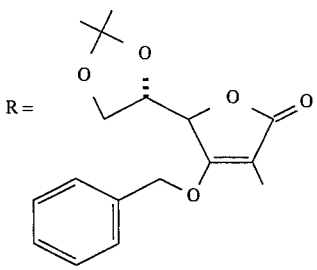

$H_3C-(CH_2)_{17}-CH(-CH_2OCH_2CH_2-OR)_2$

Starting material

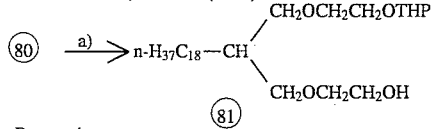

J. Skarzewski, J. Mlochowski
Tetrahedron 39, 309–312 (1983)

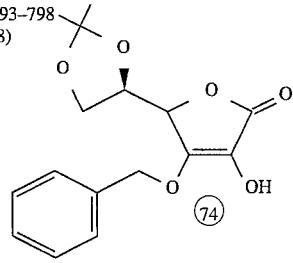

Preparation
J. Med. Chem.
31, 793–798
(1988)

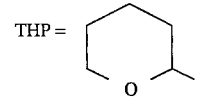

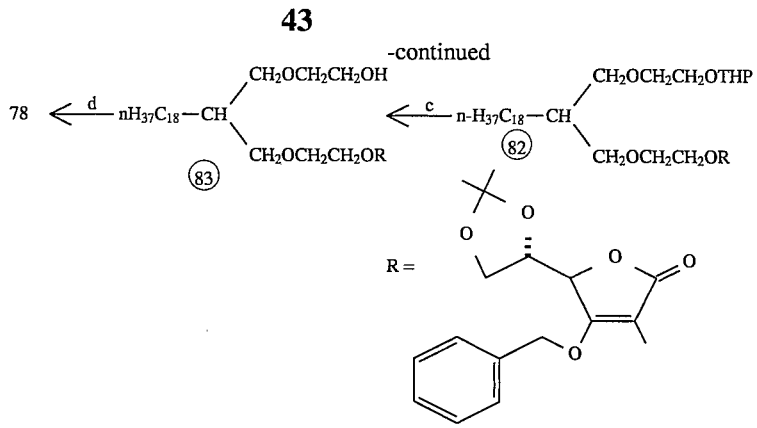

EXAMPLE 81 FROM 80 (a)

5 g (0.012 mol) of diol 81 were dissolved in 25 ml of dichloromethane, and 1.1 ml (0.012 mol) of dihydropyran and 500 mg of pyridinium p-toluenesulfonate were added. After stirring at room temperature for 6 h, the mixture was diluted with 100 ml of ether and washed with saturated sodium chloride solution (2x). The organic phase was dried and evaporated. Chromatography on silica gel (ethyl acetate/cyclohexane=1:1) gave 3.1 g (52%) of Example 81 in addition to 1.53 g of bis-THP ether and 1.0 g of starting material.

EXAMPLE 82 FROM 81 (b)

2.75 g (5.5mmol) of Example 81, 1.68 g (5.5mmol) of 74, 1.44 g (5.5 mmol) of triphenylphosphine and 1.1 ml. (5.5 mmol) of diisopropyl azodicarboxylate in 25 ml of THF were stirred at room temperature for 1 h. After evaporation, the residue was chromatographed on silica gel (ethyl acetate/cyclohexane=1:2). Yield 2.3 g (53%) of Example 82.

EXAMPLE 83 FROM 82 (c)

70 mg of pyridinium p-toluenesulfonate were added at room temperature to 2.2 g (2.8mmol) of Example 82 in 50 ml of ethanol and the mixture was stirred at 50° C. for 4 h. The reaction mixture was evaporated and the residue was partitioned between ether and semisaturated NaCl solution. Drying of the organic phase (MgSO$_4$) and evaporation gave, after chromatography on silica gel (cyclohexane/ethyl acetate=1:1), 1.3 g (67%) of Example 83.

EXAMPLE 78 FROM 83 (d)

Analogously to Example 82 (b).

EXAMPLE 79

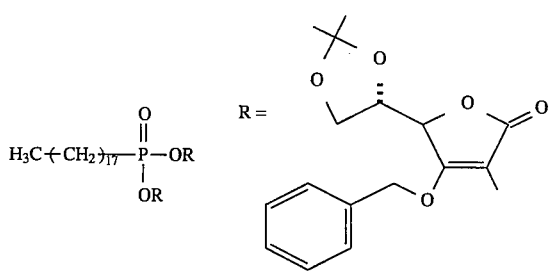

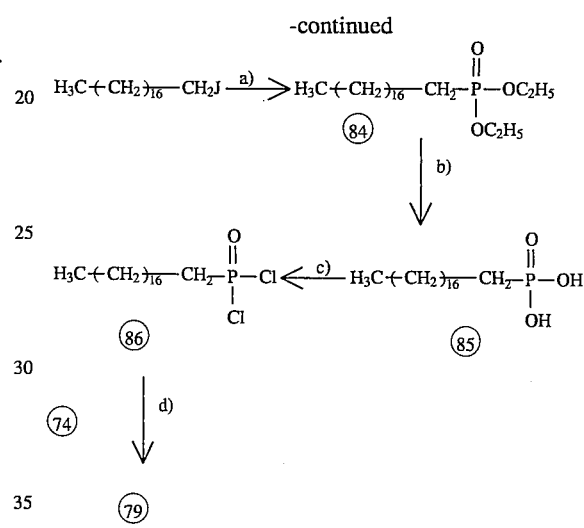

EXAMPLE 84 a)

17.5 g (46 mmol) of octadecyl iodide and 8.0 ml (46 mmol) of triethyl phosphite were heated under reflux for 2 h. Chromatography on silica gel (ethyl acetate) gave 12.2 g (31 mmol, 68%) of Example 84.

EXAMPLE 85 b)

The hydrolysis of 84 to give 85 was carried out by boiling with concentrated hydrochloric acid for several hours (TLC checking) and the product was worked up in the customary manner.

EXAMPLE 86 (c)

1 g of acid Example 85 was boiled under reflux for 2 h in 20 ml of thionyl chloride with the addition of a drop of DMF. Concentration and evaporation several times with toluene gave the acid chloride 86.

EXAMPLE 79 (d)

The reaction was carried out analogously (2 equivalents of 74) to Example 75 (procedure a). Extractive work-up and chromatography on silica gel (cyclohexane/ethyl acetate= 3:2, 1:1) gave Example 79. Yield 54%.

EXAMPLES 36 AND 37

Example 36 was obtained from Example 78 and Example 37 from Example 79 analogously to Example 75 (procedure b) and Example 34.

EXAMPLE 36

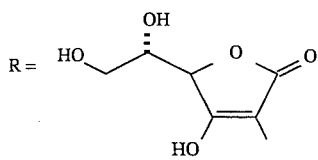

$H_3C-(CH_2)_{17}-CH-(CH_2OCH_2CH_2-OR)_2$ m.p. > 120° C. (dec.)

$C_{37}H_{64}O_{14}$ (732), MS (FAB, 3-NBA/LiI): 751 (M+3Li-2H)

EXAMPLE 37

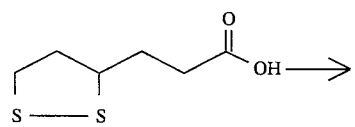

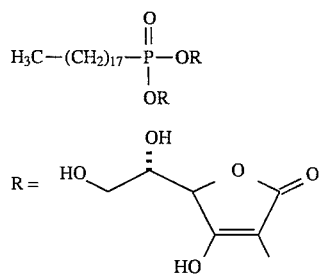

m.p. 72°–75° C.
$C_{30}H_{51}O_{13}P$ (650), MS (DCI): 651 (M+H$^+$)

EXAMPLES 46–55 a) Preparation of lipoic acid esters

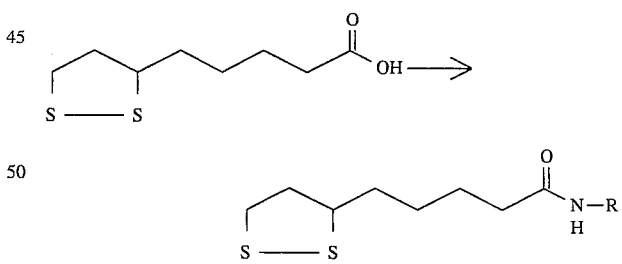

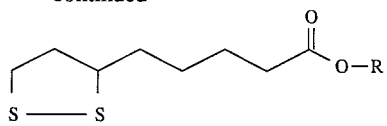

Lipoic acid and the appropriate alcohol are initially introduced into dichloromethane in a molar ratio of 1:1. 1 equivalent of 4-dimethylaminopyridine and then 1 equivalent of dicyclohexylcarbodiimide are added at room temperature. The mixture is stirred at room temperature for 2–5 h and evaporated, the product is taken up in a suitable solvent (the urea for the largest pan usually remains undissolved) and the solution is chromatographed on silica gel.

The lipoic acid esters shown in Table 3 were obtained by the process.

TABLE 3

| Example | R | MS |
|---|---|---|
| 53 | (cholesteryl group) | $C_{35}H_{58}O_2S_2$ (574) MS (DCI): 575 (M + H$^+$) |
| 51 | $-(CH_2)_{17}CH_3$ | $C_{26}H_{50}O_2S_2$ (458) MS (DCI): 458 | b) Preparation of lipoic acid amides

Lipoic acid and the corresponding amine are initially introduced into dichloromethane in a molar ratio of 2:1 or 1:1. 1 equivalent of 4-dimethylaminopyridine and then 1 equivalent of dicyclohexylcarbodiimide are added at room temperature. The mixture is stirred at room temperature for 2–5 h and evaporated, the product is taken up in a suitable solvent (the urea for the largest part usually remains undissolved) and the solution is chromatographed on silica gel.

The lipoic acid amides shown in Table 4 were obtained according to this process.

TABLE 4

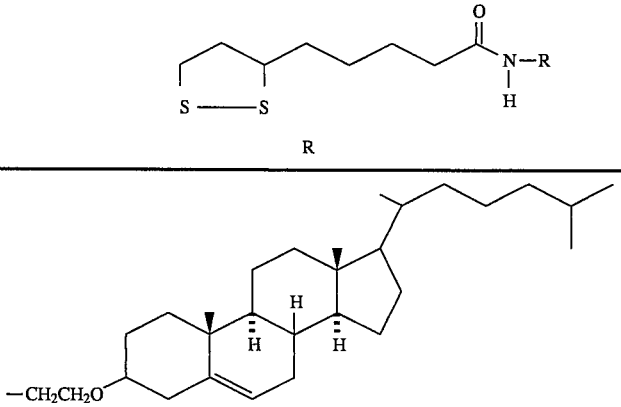

| Example | R | MS |
|---------|---|----|
| 54 | 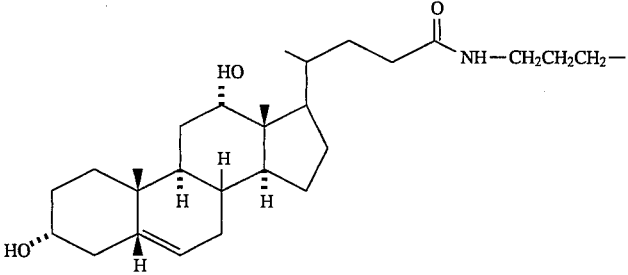<br>—CH₂CH₂O— [steroid/cholesterol group] | $C_{37}H_{63}NO_2S_2$ (618)<br>MS (FAB, 3-NBH/<br>LiJ): 624 (M + Li⁺) |

(Starting amine by Gabriel synthesis from 71 via the corresponding iodide)

| | | |
|---|---|---|
| 55 | 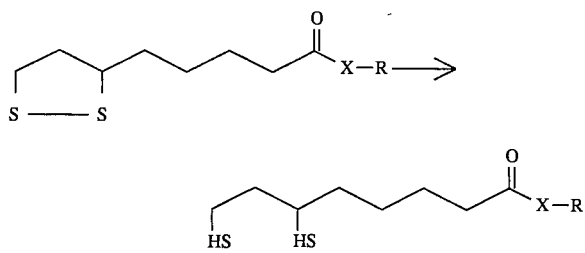 | see 48 |
| 52 | —(CH₂)₁₇CH₃ | $C_{26}H_{51}NOS_2$ (457)<br>MS (DCI): 458<br>(M + H⁺) | c) Reduction of lipoic acid derivatives to dihydrolipoic acid derivatives

[Reaction scheme: lipoic acid derivative with disulfide (S—S) and C(=O)X—R reduced to dihydrolipoic acid derivative with two HS groups and C(=O)X—R]

X = O, NH 1 part of lipoic acid derivative is initially introduced in methanol/THF mixtures (preferably 1:2) and 2–3 equivalents of sodium borohydride are added at 0° C. under a nitrogen atmosphere. After stirring at 0° C. for 2–3 h, the mixture is poured into semisaturated ammonium chloride solution and extracted using ethyl acetate (2x). The combined organic phases are dried (MgSO₄) and evaporated. The product is dried in a high vacuum.

The examples of Table 5 were prepared by this process.

TABLE 5

$$\underset{\underset{HS}{}\ \underset{SH}{}}{\diagdown}\diagdown\diagdown\diagdown\overset{O}{\underset{\|}{C}}-X-R$$

| Example | R | MS |
|---|---|---|
| X = O | | |
| 46 | (cholesterol structure) | $C_{35}H_{60}O_2S_2$ (576)<br>MS (FAB, 3-NBA/LiJ): 583<br>$(M+H^+)$ |
| 50 | $-(CH_2)_{17}CH_3$ | $C_{26}H_{52}O_2S_2$ (460)<br>MS (DCI): 461<br>$(M+H^+)$ |
| X = NH | | |
| 47 | (cholesteryl -H₂CH₂CO- structure) | $C_{37}H_{65}NO_2$ (619)<br>MS (FAB, 3-NBA/LiJ): 626<br>$(M+Li)$ |
| 48 | (dihydroxy steroid-NH-CH₂CH₂CH₂-) | $C_{35}H_{62}N_2O_4S_2$ (638)<br>MS (FAB, 3-NBA/LiJ): 645<br>$(M+Li^+)$ |
| 49 | $-(CH_2)_{17}CH_3$ | $C_{26}H_{53}NOS_2$ (459)<br>MS (DCI): 460<br>$(M+H^+)$ |

Lipophilic and Antioxidative Properties

Method I

Antioxidative radical scavenger properties by the diphenylpicrylhydrazine (DPPH) method: The determination was carried out spectrophotometrically (PMQ4 from Zeiss, Oberkochen, FRG) by the method described in Smith and Reeves, Biochemical Pharmacology 36 (1987) pp. 1457–1460. The antioxidative effects of the preparations tested are shown in Table 1. The measurement is the rate constant determined graphically (concentration versus conversion rate) in a known manner, measured in absolute ethanol. With the exception of the oxidized mercaptans, all preparations investigated in fact showed variously pronounced, but clear antioxidative action.

Method II

Use as an additive in frying fat: Samples of commercially available German non-blended butter were melted and in each case 1% (weight/weight) of BHT (=butylated hydroxytoluene) or 2,6-di-tert.-butyl- 4-(7-nonynoyl)-phenol [=compound according to Example 17] or ethyl 2-(3,5-di-tert.-butyl-4-hydroxybenzyl)- 3-oxo-docosanoate [=compound according to Example 18] or N-octadecyl-DL-α-lipoic acid amide [=compound according to Example 52] was added and the mixture was used in the customary manner as frying fat. After the frying procedure, the sample containing BHT was transformed into a viscous, dark brown material, while the use of said comparison preparations led to a substantially lower color change. The better protective action of the comparison preparations probably comes about as a result of their lipophilic side chains and, therefore, improved lipophilic interaction. The advantageous action of N-octadecyl-DL-α-lipoic acid amide is particularly surprising, although this preparation has no recognizable antioxidative component.

Method III

Lipid solubility of the compounds and protective action.

a) Preparation of olive oil or aqueous solutions. 1 ml of olive oil or 1 ml of double-distilled water (or dilute NaOH pH=7.6) was added to 1 mg or 10 mg or 50 mg of the respective compound at 37° C. and it was checked whether a clear solution was obtained. The optionally centrifuged and decanted olive oil solutions were heated for 5 minutes using a Bunsen burner and the degree of browning of the olive oil was determined. Under these conditions, the oil without additive and without protective action becomes distinctly dark brown. After addition of antioxidant and in the case of good protective action, the oil becomes only dark yellow to light brown. Samples having poor protective action are given a (*) in the table (see below).

The extremely high solubility (>1:1) of the antioxidants according to the invention in molten cholesteryl palmirate at 85° C. is also advantageous.

TABLE 1

| Compounds tested: | Results Method I Reaction with DPPH (rate constant) | Method III Solubility (mg/ml) Water | Olive oil |
|---|---|---|---|
| Vitamin E analogues | | | |
| 6-Hydroxy-2,5,7,8-tetra-methylchroman-2-carboxylic acid[1] | 2.65 | >10.0 | <0.1 |
| Vitamin E[1] | 2.90 | <0.1 | >10.0 |
| Cpd. acc. to Ex. 1 | 0.681 | >0.1 | >10.0 |
| Cpd. acc. to Ex. 2 | 0.528 | >0.1 | >10.0 |
| Cpd. acc. to Ex. 3 | | <0.1 | >1.0 |
| Vitamin E analogues | | | |
| 6-Hydroxy-2,5,7,8-tetra-methylchroman-2-carboxylic acid[1] | 2.65 | >10.0 | <0.1 |
| Vitamin E[1] | 2.90 | <0.1 | >10.0 |
| Cpd. acc. to Ex. 4 | | >0.1 | >10.0 |
| Cpd. acc. to Ex. 5 | | <0.1 | >10.0 |
| Cpd. acc. to Ex. 6 | 0.254 | <0.1 | >10.0 |
| Cpd. acc. to Ex. 7 | 0.355 | <0.1 | >10.0 |
| Cpd. acc. to Ex. 8 | | <0.1 | >10.0 |
| Phenols | | | |
| Gallic acid[1] | | >10.0 | <0.1 |
| BHT[1] | | <0.1 | >10.0 |
| Cpd. acc. to Ex. 13 | 0.061 | <0.1 | >50.0 |
| Cpd. acc. to Ex. 17 | 0.004 | <0.1 | >50.0 |
| Cpd. acc. to Ex. 18 | | <0.1 | >50.0 |
| Cpd. acc. to Ex. 19 | 0.268 | <0.1 | >50.0 |
| Cpd. acc. to Ex. 20 | | <0.1 | >50.0 |
| Cpd. acc. to Ex. 21 | 0.236 | <0.1 | >50.0 |
| Cpd. acc. to Ex. 22 | 0.004 | <0.1 | >50.0 |
| Cpd. acc. to Ex. 23 | 0.006 | <0.1 | >50.0 |
| Cpd. acc. to Ex. 24 | 0.054 | <0.1 | >50.0 |
| Cpd. acc. to Ex. 25 | 0.052 | <0.1 | >50.0 |
| Cpd. acc. to Ex. 26 | 0.065 | <0.1 | >50.0 |
| Cpd. acc. to Ex. 27 | | >10.0 | >1.0 |
| Cpd. acc. to Ex. 28 | | <0.1 | >50.0 |
| Cpd. acc. to Ex. 29 | 0.711 | >1.0 | >10.0 |
| Ascorbic acid analog | | | |
| Ascorbic acid[1] | 2.99 | >10.0 | <0.1 |
| Ascorbyl palmitate[1] | | <0.1 | >0.1 |
| Cpd. acc. to Ex. 34 | 0.052 | <0.1 | >1.0 |
| Cpd. acc. to Ex. 35 | 0.053 | <0.1 | >1.0 |
| Cpd. acc. to Ex. 37 | 1.13 | >10.0 | >1.0 |
| Cpd. acc. to Ex. 33 | | <0.1 | >1.0 |
| Cpd. acc. to Ex. 36 | 0.242 | >10.0 | >10.0 |
| Mercaptans | | | |
| Dihydrolipoic acid, Na salt[1] | 3.147 | >10.0 | <0.1* |
| Dithioerythritol[1] | 5.632 | >10.0 | <0.1 |
| Dithioerythritol[1] | | >10.0 | <0.1 |
| 2,3-Mercaptosuccinic acid[1] | | >10.0 | <0.1 |
| Cpd. acc. to Ex. 46 | 0.440 | <0.1 | >50.0 |
| Cpd. acc. to Ex. 47 | 0.075 | <0.1 | >50.0 |
| Cpd. acc. to Ex. 48 | 0.337 | <0.1 | >50.0 |
| Cpd. acc. to Ex. 49 | 0.243 | <0.1 | >10.0 |
| Cpd. acc. to Ex. 50 | 0.248 | <0.1 | >50.0 |
| Oxidized Mercaptans | | | |
| Lipoic acid, Na salt[1] | 0.0 | >10.0 | <0.1* |
| Cpd. acc. to Ex. 51 | 0.0 | <0.1 | >50.0 |
| Cpd. acc. to Ex. 52 | 0.0 | <0.1 | >10.0 |
| Cpd. acc. to Ex. 53 | | <0.1 | >50.0 |

[1] = not according to the invention

Result

In addition to the required lipid solubility, the antioxidants according to the invention show excellent antioxidative protective effects.

The findings of Table 1 were supplemented by the experimental determination of the partition coefficient $K_d$ (butanol/water method according to Carney and Graham, Arzneim.-Forschung 35 (1985) 228–233), which confirmed the lipophilicity of the compounds.

It was also possible experimentally to extract virtually completely (to about 100%) the compounds according to the invention from aqueous solutions or suspensions (consisting of 1 mg of antioxidant/ml of physiological saline solution pH=7.6) by octanol.

Owing to its solubility properties, the compound according to Example 36 is outstandingly suitable for use in aqueous oil emulsions.

Method IV

Inhibition of the oxidation of lipids

Oxidation of 1-stearoyl-2-arachidonoylphosphatidylcholine (SA-PC) in cyclohexane (37° C.). 100 mcl of a SA-PC solution (10 mg/ml of $CHCl_3$) were evaporated by blowing (argon) and the residue was taken up in 1 ml of cyclohexane. After adding an amount of antioxidant which would also dissolve in olive oil (cf. Table 1), the absorption was measured at 234 nm (Perkin Elmer 5528 spektrophotometer, Überlingan, FRG) and the solvent was then evaporated by blowing with air. After a fur%her 24 hours standing in an open vessel, the residue was again dissolved in i ml of cyclohexane and the absorption at 234 nm was measured as a measurement of the oxidized SA-PC.

Result

Owing to their good lipid solubility, it was possible to suppress virtually completely the oxidation of SA-PC with 1 mg to 10 mg/ml of the antioxidants according to the invention in each case. It was surprisingly possible to prevent the oxidation of SA-PC Just as effectively with the reduced dithiol compounds according to the invention (Examples 49 and 50) as with the corresponding oxidized dithio compounds (Examples 51 and 52 without free SH groups).

Method V

Inhibiting effect on fatty acid oxidation in rat mitochondria (Malonaldehyde determination by the thiobarbiturate method according to Ottolenghi, Arch. Biochem. Biophys. 79 (1959) pp. 355 et seq.). The determination was carried out spectrophotometrically in mitochondrial homogenates from rats. The inhibition of fatty acid oxidation by the preparations according to the invention was virtually complete.

Method VI

Inhibition of lipid oxidation in liposomal biomembranes

An aqueous solution of liposomes (Nattermann, Cologne/Germany) was diluted with double-distilled water until the absorption measured at 234 nm against air in a spectrophotometer (PMQ II from Zeiss, Oberkochen/Germany) was between 0.25 and 0.35 (corresponds to about 0.1 mg of liposomes/ml). 50 mcmol/l of cumene hydroperoxide and 12 mcmol of hematin were then added to this liposome suspension (total volume 1 ml) and the increase in the absorption at 234 nm was monitored periodically as a measure of the rate of liposome oxidation.

It was possible to suppress the oxidation of the liposomes by addition of the antioxidants according to the invention. The following table shows the mean increase in $\Delta E_{234}$/min in batches with and without antioxidant after 25 min at 25° C.

TABLE

| | $\Delta E_{234}$/min |
|---|---|
| without addition of antioxidant | 0.035 |
| with addition of 100 nmol/l of antioxidant according to the invention | 0.005 |
| to | 0.015 |

Even better results are obtained if the lipophilic antioxidants are additionally incorporated during the preparation of the liposomes as components thereof.

Method VII

Inhibition of LDL oxidation according El-Saadani et al., Journal of Lipid Research 30 (1989) page 627

Analogously to method VI, the lipophilic antioxidants also protect "Low-Density Lipoprotein" (Sigma, St. Louis, U.S.A.) from oxidation.

Method VIII

Laser-induced thrombosis in rats in vivo

The experimental procedure was carried out in every detail as described in U.S. Pat. No. 4,694,024. Laser induction took place 60 min after oral administration of the antioxidants. After oral administration of the antioxidants according to the invention (30 mg/kg), a significantly higher number of laser pulses was necessary than in the comparison experiments, i.e. the thrombosis inhibiting power of resistance of the animals was higher after administration of the antioxidants according to the invention.

| | Reduction of thrombus formation |
|---|---|
| Compound acc. to Example 13 | 17% |
| Compound acc. to Example 52 | 14% |
| Compound acc. to Example 49 | 20% |
| Compound acc. to Example 47 | 15% |
| Compound acc. to Example 3 | 11% |
| Compound acc. to Example 2 | 14% |
| Compound acc. to Example 1 | 16% |
| Compound acc. to Example 36 | 17% |
| Compound acc. to Example 33 | 13% |
| (4,4'-(Isopropylidene-dithio)bis[2,6-di-tert.-butylphenol] | 6% |
| Vitamin E | 5% |

Method IX

Photochemically-induced thrombus formation in rats in vivo

The measurements were carried out on mesenterial arterioles. To this end 0.3 ml of a solution of fluorescein lsothiocyanate-dextran 70 (FITC-Dextran, Sigma, Seidenhofen, FRG) was injected, and the arterioles were then irradiated with light (490 nm) in the observation field. The thrombi formed as a result were quantified by vital microscopy, as described under Method VIII. Using antioxidants according to the invention, it was possible to inhibit the thrombus formation one hour after oral administration of 50 mg/kg of rat body weight by up to 20%.

Method X

Arachidonic acid-induced platelet aggregation according to Ruppert and Weithmann, Life Sciences 31 (1982) 2037 et seq.

The antithrombotic effect of the substances according to the invention has not come about as a result of an inhibition of platelet aggregation, since no significant inhibitory action was to be detected up to 10 mcmol/l of the substances according to the invention. Thus, an increased proneness to bleeding of patients who are treated with these substances is not expected.

Method XI

Effect of the compounds according to the invention on long-term administration in the hyperlipidemic infarct-sensitive rat:

Male infarct-sensitive rats about 200 g in weight (M öllegaard, Ejby, Denmark) were treated orally once daily with 1 ml/100 g of body weight of a standard diet (100 g of cholic acid, 100 g of cholesterol, 30 g of propylthiouracil to 1 l of sesame oil). While no test substance was administered to the control group I (cf. the following Table), the standard diet in the pharmaceutical experiments II–IV additionally contained 50 mg/kg of body weight of the test substances indicated in the table below. After 9 days, the rats were examined, as described above, in the laser-induced thrombosis test, and the total cholesterol content of the serum was determined. It can be seen from the following table that the proneness to thrombosis of the hyperlipidemic infarct-sensitive rats in comparison to healthy rats (<100 mg of cholesterol/dl) can be treated with the substances according to the invention surprisingly more successfully than with vitamin E. Moreover, the substances according to the invention exerted an advantageous hypolipidemic effect.

| Group | Number of animals n = | Total cholesterol mg/dl | Reduction in proneness to thrombosis vs. control (%) |
|---|---|---|---|
| I Control | 5 | 286 | — |
| II Vitamin E | 6 | 278 | 26 |
| III Compound according to Example 2 | 4 | 270 | 50 |
| IV Compound according to Example 49 | 5 | 259 | 34 |

We claim:

1. A compound of the formula I $$(A)_a(L)(X)_{a'}, \quad (I)$$

in which a and a' independently of one another are 1 or 2,

A is an antioxidative component selected from the group consisting of $A_2$—an alkyl-substituted mono-, di- or triphenol radical

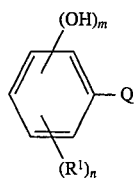

in which m is 1 or 2, n is 1 or 2, and m+n is 3 or 4, $R^1$ is the same or different and is an alkyl radical or an alkoxy radical and the total number of carbon atoms of the alkyl and alkoxy radicals is a maximum of 8, $A_3$—a reductone radical

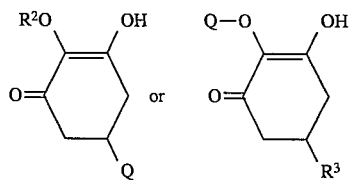

in which $R^2$ is H or a lower alkyl radical and $R^3$ is H, $COOR^4$ or $CH_2OR^4$ in which $R^4$ is H or a lower alkyl radical, $A_4$—a 1,2-dithiacycloalkyl or 1,2-dithiacycloalkenyl radical having 2–6 carbon atoms in the ring or the dithiol form of these radicals which has been reduced by hydrogenation, and $A_5$—an ascorbic acid radical or derivative thereof

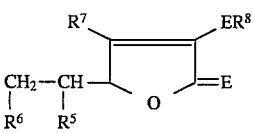

in which

E is O, S or $NR^9$ $R^5$ is H, EH, EQ or Q $R^6$ is H, EH, EQ—(L—$X_1$) or Q—(L—$X_1$)

$R^7$ is H, EH, EQ, Q or one of the radicals defined above as $A_2$ or $A_3$ $R^8$ is H, EH, Q—(L—$X_1$) or —PO(OR$^9$)$_2$, $R^9$ is a lower alkyl radical or Q, and only one or two of the radicals $R^5$–$R^9$ are identical to Q or contain Q, L is a bridging member as defined below and $X_1$ is a lipophilic component as defined below;

L is a bridging member composed of one or more of the building blocks of the following formulae

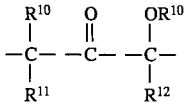

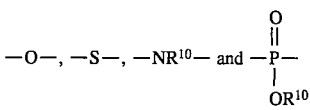

in which $R^{10}$, $R^{11}$ and $R^{12}$ are H, a lower alkyl radical or Q, or in which $R^{11}$ is —CO$_a$R$^{10}$ wherein a is 1 or 2, and 2 radicals selected from the group consisting of —O—, —S— and —NR$^{10}$— are separated from one another by at least one carbon or phosphorus atom; and X is a lipophilic component selected from the group consisting of $X_1$—a cholane derivative radical, of the following formula

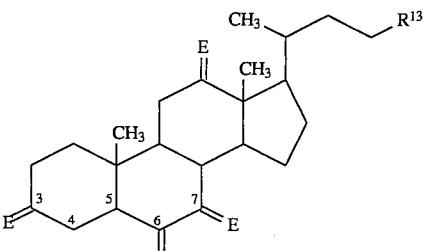

in which $R^{13}$ is sec. $C_4H_9$, $R^{11}$ as defined in L or Q,

E is O, S, NR$^{10}$ as defined in L, α,β-OH, H or α,β-Q, H and a double bond can be present in the 4,5- or 5,6- or 7,8-position, and $X_2$—an alkyl or cycloalkyl radical or a fatty acid derivative radical having up to 24 carbon atoms and Q in all the above formulae represents a free valency (covalent single bond).

2. A compound of the formula I as claimed in claim 1, wherein the component $A_4$ is a radical of the following formulae in the dithia form or in the dithiol form which has been reduced by hydrogenation:

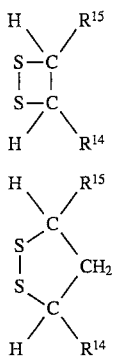   A₄.₁

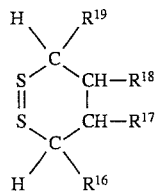   A₄.₂ in which $R^{14}$ is H or a lower alkyl radical and $R^{15}$ is —(CH₂)$_b$—Q wherein b is 0–12,

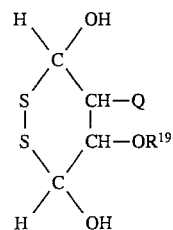   A₄.₃ in which $R^{16}$ and $R^{19}$ are independently of one another H or a lower alkyl radical $R^{17}$ is Q and $R^{18}$ is H, a lower alkyl radical, an acyl radical OCOR¹⁹ or OR¹⁹

$R^{19}$ is a lower alkyl radical or Q, A₄.₄ a dithiothreitol or dithioerythritol partial structure

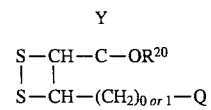

in which $R^{19}$ has the same meaning as in 4.3,

```
    Y
    |
S—CH—C—OR²⁰
|   |
S—CH—(CH₂)₀ ₒᵣ ₁—Q
```
A₄.₅ in which $R^{20}$ is H or a lower alkyl radical and Y is H₂ or O.

3. A compound of the formula I as claimed in claim 2, wherein in the component

A₄.₂, $R^{14}$ is H and $R^{15}$ is —(CH₂)₄—Q.

4. A compound of the formula I as claimed in claim 1, wherein in the structural radical A₅, $R^7$ is

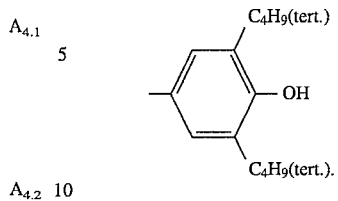

5. A compound of the formula I as claimed in claim 1, wherein in the structural radical A₅, E is O $R^5$, $R^6$ and $R^7$ independently of one another are OH or OQ, R is H or Q, where only one or two of the radicals $R^5$–$R^8$ contain Q or are equal to Q.

6. A compound of the formula I as claimed in claim 1, wherein the bridging member L is $M_p$ {[—CH₂)$_w$—(G₁)$_x$—(G₂)]$_v$—(CH₂)$_y$— (G₃)$_z$— (G₄)$_{p+1}$}$M_p$ in which p, x and z independently of one another are 0 or 1, v, w and y independently of one another are 0–4, and v+w+y+z is 0–10, M is —CR¹⁰=, —N= or

G₁, G₂, G₃ and G₄ independently of one another are —O—, —S—, —NR¹⁰—,

—CHOR¹⁰— or —CH(CH₂—OR¹⁰)—, where $R^{10}$ has the meaning as defined in claim 1 and two of the radicals —O—, —S— and —NR¹⁰— are separated from one another by at least one carbon atom.

7. A compound of the formula I as claimed in claim 1, wherein the bridging member L is a radical selected from the group consisting of:

L₁: Q—O—(CH₂)$_r$—O—CO—Q

L₂: Q—CO—NH—(CH₂)$_q$—NH—CO—Q

L₃: Q—O—(CH₂—)$_r$—NH—CO—Q

L₄: Q—(CH₂—)$_r$(—O—)$_b$—Q

L₅: Q—(CH₂—)$_s$—O—(CH₂—)$_r$—O—Q

L₆: Q—(CH₂—)$_s$—NH—(CH₂—)$_r$—O—Q

L₇: Q—CO—NH—(CH₂—CH₂)$_r$—O—Q

L₈: Q—O—(CH₂—)$_s$—CHOH—(CH₂—)$_s$—O—(CH₂—)$_s$—Q

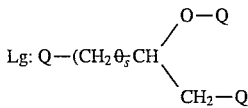

L₁₀: Q—(CH₂—)$_q$—Q

L₁₁: Q—(CH₂—)$_s$—CHCO₂R¹⁰—CHOH—Q

L₁₂: Q—CH=C(CO₂R¹⁰)—CO—Q

L₁₃: Q—CO—NH—(CH₂—)$_q$—NH—CO—Q $L_{14}$: Q—(CH$_2$—)$_s$—O—(CH$_2$—)$_r$—O—

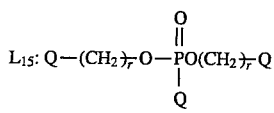

$L_{16}$: [Q—(CH$_2$—)$_2$—O—(CH$_2$)$_s$ ]$_2$CH—Q
$L_{17}$: Q—O—(CH$_2$—)$_s$—CHOH—O—(CH$_2$—)$_s$—Q
$L_{18}$: Q—O—(CH$_2$—)$_s$—CH(CH$_2$—OH)—O—CO—Q
$L_{19}$: Q—O—(CH$_2$—)$_s$—CHOH—(CH$_2$—)$_s$—O—CO—O
$L_{20}$: Q—CO—NR$^{10}$—Q
$L_{21}$: Q—CO(O)$_x$—Q
$L_{22}$: Q—CH$_2$—N[CH(CH$_3$)$_2$]—(CH$_2$)$_r$—CHOHCH$_2$CHOHCH$_2$—CO(O)$_x$—Q
$L_{23}$: Q—(CH$_2$)$_s$—Q
$L_{24}$: Q—NR$^{10}$—Q
$L_{25}$: Q—O—Q
$L_{26}$: Q—(CH$_2$)$_s$—CHCO$_2$R$^{10}$—SOQ

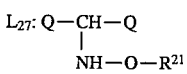

in which R$^{21}$ is benzyl or R$^{10}$, and

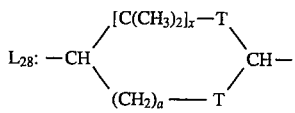

in which
T is O or S
x is 0 or 1
a is 1 or 2; and
q is 1–5,
r is 1–5,
s is 1–5,
and R has the meaning as defined in claim 1.

8. A compound of the formula I as claimed in claim 1, wherein the lipophilic component X is a radical selected from the group consisting of:
$X_{1.1}$ cholesterol
$X_{1.2}$ cholestanol
$X_{1.3}$ cholic acid
$X_{1.4}$ desoxycholic acid
$X_{1.5}$ ursodesoxycholic acid and
$X_{1.6}$ chenodesoxycholic acid.

9. A compound of the formula I as claimed in claim 1, wherein the lipophilic component X is a radical selected from the group consisting of:
$X_{2.1}$ CH$_3$—(CH$_2$)$_t$—Q
$X_{2.2}$ Q—C(CH$_3$)$_3$
$X_{2.3}$ Q—CH(CH$_2$)$_d$
$X_{2.4}$ Q—C=C—(CH$_2$)$_5$—CH$_3$
$X_{2.5}$ R$^{10}$—CO$_2$(CH$_2$)$_z$—Q
d is 4–6
t is 3–24, and
z is 0 or 1.

10. A method of treating a host affected by a disease involving bioradicals which comprises administering to said host a compound of formula I as claimed in claim 1.

11. A method of treating a host affected by a disease involving bioradicals as claimed in claim 10, wherein said disease is a coronary, circulatory or vascular disease.

12. A pharmaceutical composition for treating a disease involving bioradicals which comprises an effective amount of the compound of the formula I as claimed in claim 1, and a pharmacologically tolerable excipient.

13. A method of treating a host affected by a disease involving bioradicals as claimed in claim 10 wherein said disease involving bioradicals is thrombosis.

* * * * *

UNITED STATES PATENT AND TRADEMARK OFFICE
CERTIFICATE OF CORRECTION

PATENT NO. : 5,508,275
DATED : April 16, 1996
INVENTOR(S) : Klaus-Ulrich WEITHMANN et al.

It is certified that error appears in the above-indentified patent and that said Letters Patent is hereby corrected as shown below:

Claim 1, column 56, line 63, after "atoms" insert --;--.

Claim 2, column 57, line 19, after "radical" insert --,--.

Claim 2, column 57, lines 24-30, the formula:

" 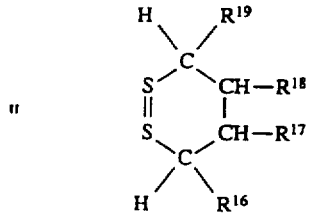   " should read -- 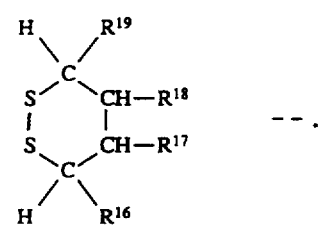 --.

Claim 7, column 58, lines 58-61,

" 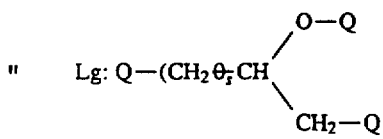   " should read -- 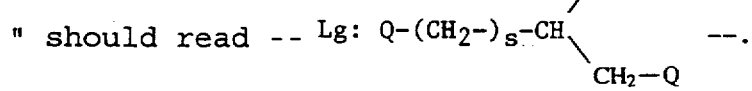 --.

UNITED STATES PATENT AND TRADEMARK OFFICE
CERTIFICATE OF CORRECTION

PATENT NO. : 5,508,275
DATED : April 16, 1996
INVENTOR(S) : Klaus-Ulrich WEITHMANN et al.

It is certified that error appears in the above-indentified patent and that said Letters Patent is hereby corrected as shown below:

Claim 7, column 59, lines 3-6,

" $L_{15}: Q-(CH_2)_{\overline{r}}O-\underset{\underset{Q}{|}}{\overset{\overset{O}{\|}}{P}}O(CH_2)_{\overline{r}}Q$ " should read -- $L_{15}: Q-(CH_2-)_r-O-\underset{\underset{Q}{|}}{\overset{\overset{O}{\|}}{P}}O(CH_2-)_r-Q$ --.

Claim 7, column 60, line 2, "R" should read --$R^{10}$--.

Claim 9, column 60, line 22, "$X_{2.5} R^{10}-CO_2(CH_2)_z-Q$" should read --$X_{2.5} R^{10}-CO_2-(CH_2)_z-Q$--.

Signed and Sealed this

Twenty-sixth Day of November 1996

Attest:

BRUCE LEHMAN

Attesting Officer     Commissioner of Patents and Trademarks